(12) United States Patent
Zou et al.

(10) Patent No.: US 11,020,333 B2
(45) Date of Patent: Jun. 1, 2021

(54) ORGANIC COMPOUNDS

(71) Applicant: Givaudan SA, Vernier (CH)

(72) Inventors: Yue Zou, Shanghai (CN); An Chai, Shanghai (CN); Jie Liu, Shanghai (CN); Lijun Zhou, Shanghai (CN)

(73) Assignee: GIVAUDAN S.A., Vernier (CH)

(*) Notice: Subject to any disclaimer, the term of this patent is extended or adjusted under 35 U.S.C. 154(b) by 149 days.

(21) Appl. No.: 16/321,653

(22) PCT Filed: Aug. 14, 2017

(86) PCT No.: PCT/EP2017/070593
§ 371 (c)(1),
(2) Date: Jan. 29, 2019

(87) PCT Pub. No.: WO2017/191331
PCT Pub. Date: Nov. 9, 2017

(65) Prior Publication Data
US 2020/0330346 A1 Oct. 22, 2020

(30) Foreign Application Priority Data
Aug. 15, 2016 (WO) ................ PCT/CN2016/095273

(51) Int. Cl.
A61K 8/18 (2006.01)
A61Q 13/00 (2006.01)
A61K 8/00 (2006.01)
A61K 8/35 (2006.01)
A61L 9/01 (2006.01)
C11B 9/00 (2006.01)
C11D 3/50 (2006.01)

(52) U.S. Cl.
CPC ........ A61K 8/35 (2013.01); A61L 9/01 (2013.01); A61Q 13/00 (2013.01); C11B 9/0049 (2013.01); C11D 3/50 (2013.01); A61K 2800/10 (2013.01)

(58) Field of Classification Search
CPC ......... A61L 9/01; A61Q 13/00; C11B 9/0049; A61K 8/35; A61K 2800/10; C11D 3/50
USPC ............................................ 512/15, 14, 8, 1
See application file for complete search history.

(56) References Cited

U.S. PATENT DOCUMENTS

| 3,944,679 A | 3/1976 | Takahara et al. |
|---|---|---|
| 5,455,365 A | 10/1995 | Winter et al. |
| 9,890,147 B2 | 2/2018 | Siegel et al. |
| 2003/0125584 A1 | 7/2003 | Sonnenberg et al. |

FOREIGN PATENT DOCUMENTS

| EP | 0 162 465 A2 | 11/1985 | |
|---|---|---|---|
| EP | 0 582 194 B1 | 5/1998 | |
| EP | 1 310 240 A1 | 5/2003 | |
| WO | WO 97/47295 A1 | 12/1997 | |
| WO | WO 03/072533 A1 | 9/2003 | |
| WO | WO-2013034657 A1 * | 3/2013 | ........... C07C 47/225 |
| WO | WO 2014/026997 A1 | 2/2014 | |
| WO | WO 2014/096282 A1 | 6/2014 | |
| WO | 2017191331 A2 | 11/2017 | |

OTHER PUBLICATIONS

Lamboley et al, Synthesis and Properties of Conformationally Constrained Analogues of Floral-Type Odorants, 2004, Helvetica Chimca Acta—vol. 87, 1767-1793 (Year: 2004).*
Written Opinion of the Intellectual Property Office of Singapore for Application No. 11201900424S, dated Jun. 9, 2020.
Chemical Abstract Services (CAS) Registry No. 1525422-36-9, Chemical Catalog, Aurora Fine Chemicals, SciFinder.
PCT/CN2016/095273—International Search Report, dated May 25, 2017.
PCT/CN2016/095273—International Written Opinion, dated May 25, 2017.
PCT/EP2017/070593—International Search Report, dated Oct. 27, 2017.
PCT/EP2017/070593—International Written Opinion, dated Oct. 27, 2017.
Bott, Kaspar, "Carboxylic acid syntheses with 1,1-dichloroethylene. II. β-alkyl- and β-arylhydrocinnamic acids", Chemische Berichte, vol. 100, Issue 9, pp. 2791-2797, Dec. 31, 1967. (Abstract.).
Chemical Abstract Services (CAS) RN: 1533518-06-7.
Chemical Abstract Services (CAS) RN: 1526645-90-8.

(Continued)

Primary Examiner — Jessica Whiteley
(74) Attorney, Agent, or Firm — Curatolo Sidoti Co., LPA; Salvatore A. Sidoti; Floyd Trillis, III.

(57) ABSTRACT

The present invention refers to indanone derivatives of formula (I)

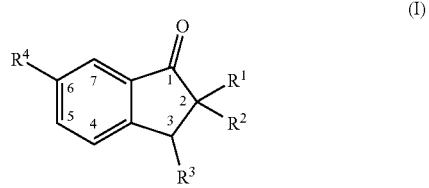

(I)

wherein
R$^1$ is selected from hydrogen, methyl and ethyl;
R$^2$ is selected from hydrogen, methyl and ethyl, and R is selected from hydrogen and methyl; or
R$^2$ and R$^3$ form together with the carbon atoms to which they are attached C$_3$-C$_5$ cycloalkyl; and
R$^4$ is selected from C$_2$-C$_5$ alkyl, C$_2$-C$_5$ alkenyl, C$_1$-C$_4$ alkoxy, C$_3$-C$_5$ cycloalkyl, and C$_3$-C$_6$ cycloalkenyl.

The invention further refers to perfume compositions and fragrance applications comprising them.

13 Claims, No Drawings

(56) References Cited

OTHER PUBLICATIONS

Chemical Abstract Services (CAS) RN: 1525557-99-6.
Chemical Abstract Services (CAS) RN: 1521067-37-7.
Chemical Abstract Services (CAS) RN: 1520396-11-5.
Chemical Abstract Services (CAS) RN: 1518376-62-9.
Chemical Abstract Services (CAS) RN: 1518118-62-1.
Chemical Abstract Services (CAS) RN: 1506054-40-5.
Chemical Abstract Services (CAS) RN: 1504005-66-6.
Chemical Abstract Services (CAS) RN: 1501421-57-3.
Chemical Abstract Services (CAS) RN: 1479064-68-0.
Chemical Abstract Services (CAS) RN: 1429243-96-8.
Chemical Abstract Services (CAS) RN: 1429238-36-7.
Chemical Abstract Services (CAS) RN: 1409714-90-4.
Chemical Abstract Services (CAS) RN: 1344902-48-2.
Chemical Abstract Services (CAS) RN: 1340024-54-5.
Chemical Abstract Services (CAS) RN: 1337850-11-9.
Chemical Abstract Services (CAS) RN: 1274508-18-7.
Chemical Abstract Services (CAS) RN: 1260010-36-3.
Chemical Abstract Services (CAS) RN: 1225517-73-6.
Chemical Abstract Services (CAS) RN: 1188167-80-7.
Chemical Abstract Services (CAS) RN: 1172804-29-3.
Chemical Abstract Services (CAS) RN: 1172261-75-4.
Chemical Abstract Services (CAS) RN: 1171645-28-5.
Chemical Abstract Services (CAS) RN: 1171541-28-8.
Chemical Abstract Services (CAS) RN: 860356-73-6.
Chemical Abstract Services (CAS) RN: 714965-15-8.
Chemical Abstract Services (CAS) RN: 663926-43-0.
Chemical Abstract Services (CAS) RN: 210759-99-2.
Chemical Abstract Services (CAS) RN: 185678-68-6.
Chemical Abstract Services (CAS) RN: 162752-17-2.
Chemical Abstract Services (CAS) RN: 162752-14-9.
Chemical Abstract Services (CAS) RN: 124688-07-9.
Chemical Abstract Services (CAS) RN: 103986-57-8.
Chemical Abstract Services (CAS) RN: 100121-78-6.
Chemical Abstract Services (CAS) RN: 42348-89-0.
Chemical Abstract Services (CAS) RN: 15954-45-7.
Chemical Abstract Services (CAS) RN: 13623-25-1.
Chemical Abstract Services (CAS) RN: 5464-10-8.

* cited by examiner

ORGANIC COMPOUNDS

CROSS REFERENCE TO RELATED APPLICATIONS

This application is a national stage application of International Application No. PCT/EP2017/070593, filed 14 Aug. 2017, which claims priority from International Patent Application No. PCT/CN2016/095273, fled 15 Aug. 2016, which applications are incorporated herein by reference.

The present invention relates to indanone derivatives possessing fruity, floral olfactory properties of high substantivity and long-lasting. The invention furthermore refers to methods for their production, and to fragrance compositions containing these.

In the fragrance and flavor industry, perfumers and flavorists are continually looking for new compounds of high impact odors, or imparting new odor notes. Fruity compounds are usually light and used as top notes in fragrance creation, so powerful and relatively less-volatile compounds in the fruity floral odor direction are of particular interest which makes them very attractive as widely used long-lasting odor notes, especially for the use in fabric care products.

Substituted indanones and indanes have been described in literature. Some have been described to be suitable as fragrance ingredients. WO03072533 A1 describes the use of 3,3-dimethyl indanones in perfumery with leathery, woody and saffron-like odors. U.S. Pat. No. 3,944,679 disclosed 2- and 3-alkyl substituted indanones imparting coumarin-like notes to tobacco, foods and drinks flavors.

Surprisingly, we have now found a new class of substituted indanones that possess very powerful and long-lasting fruity, floral notes with green facets. In particular it was surprisingly found that C-6 substituted indanone derivatives of formula (I) as defined herein below possess a remarkable low odor threshold value compared to their C-4, C-5, and C-7 substituted equivalents.

As used herein, "odor threshold value" means the lowest concentration of a vapour in the air which can be detected by smell. Generally speaking, it can be said that a compound with a low odor threshold value is more powerful than a compound with a high odor threshold value and thus allows the use of very low concentration in a fragrance composition to achieve an olfactory effect.

There is provided in a first embodiment the use as fragrance of a compound of formula (I)

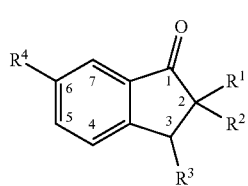

wherein
$R^1$ is selected from hydrogen, methyl and ethyl;
$R^2$ is selected from hydrogen, methyl and ethyl, and $R^3$ is selected from hydrogen and methyl; or
$R^2$ and $R^3$ form together with the carbon atoms to which they are attached $C_3$-$C_5$ cycloalkyl (e.g., cyclobutyl);
$R^4$ is selected from $C_2$-$C_5$ alkyl (including $C_3$ alkyl and $C_4$ alkyl, such as propyl, isopropyl, butyl, isobutyl, tert-butyl, sec-buty), $C_2$-$C_5$ alkenyl (such as allyl, methylallyl), $C_1$-$C_4$ alkoxy (including $C_2$ alkoxy and $C_3$ alkoxy, e.g., ethoxy, propoxy, isopropoxy, butoxy, isobutoxy), $C_3$-$C_5$ cycloalkyl (e.g., cyclopropyl, cyclopentyl), end $C_3$-$C_6$ cycloalkenyl (e.g. cyclopentenyl, cyclobutenyl).

The compounds of formula (I) comprise one or more chiral centers and as such may exist as a mixture of stereoisomers, or they may be resolved as isomerically pure forms Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art. e.g. preparative HPLC and GC, crystallization or stereoselective synthesis.

As a specific example of compounds of formula (I), one may cite, as non-limiting example, 6-isobutyl-2-methyl-2,3-dihydro-1H-inden-1-one, which possesses a very powerful, floral fruity fatty, with creamy lactonic nectaryl like facet, and a rosy floral character with rose petal like and green rose oxide like facets. 6-Isobutyl-2-methyl-2,3-dihydro-1H-inden-1-one has one chiral carbon center. Whereas both enantiomers possess very similar odor profiles, (S)-6-isobutyl-2-methyl-2,3-dihydro-1H-inden-1-one is more powerful than (R)-6-isobutyl-2-methyl-2,3-dihydro-1H-inden-1-one. As a further specific example of compounds of formula (I), one may cite, as non-limiting example, 6-(sec-butyl)methyl-2,3-dihydro-1H-inden-1-one, which is a very powerful ingredient with strong green rosy metallic and green leathery rubbery facets, and an overall fatty fruity floral character.

Further, no-limiting examples are compounds of formula (I) wherein either $R^2$ or $R^3$ is hydrogen.

Further, non-limiting examples are compounds of formula (I) wherein $R^2$ and $R^3$ are hydrogen.

Further, non-limiting examples are compounds of formula (I) wherein at least one of $R^1$, $R^2$ and $R^3$ is not hydrogen.

Further, non-limiting examples are compounds of formula (I) wherein $R^1$ is methyl.

Further, non-limiting examples are compounds of formula (I) wherein $R^1$ is methyl and $R^2$ and $R^3$ are hydrogen.

Further, non-limiting examples are compounds of formula (I) wherein $R^1$ is methyl and $R^4$ is selected from $C_2$-$C_5$, alkyl (including $C_3$ alkyl and $C_4$ alkyl, such as propyl, isopropyl, butyl, isobutyl, tert-butyl, sec-butyl), $C_2$-$C_5$ alkenyl (such as allyl, methylallyl) and $C_1$-$C_4$ alkoxy (including $C_2$ alkoxy and $C_3$ alkoxy, e.g., ethoxy, propoxy, isopropoxy butoxy, isobutoxy).

Further, non-limiting examples are compounds of formula (I) wherein $R^1$ is methyl and $R^4$ is selected from $C_3$-$C_6$ alkyl (including $C_3$ alkyl and $C_4$ alkyl, such as propyl, isopropyl butyl, isobutyl, tert-butyl), and $C_2$-$C_4$ alkoxy (including $C_2$ alkoxy and $C_3$ alkoxy, e.g., ethoxy, propoxy, isopropoxy, butoxy, isobutoxy).

Further, non-limiting examples are compounds of formula (I) wherein $R^1$ is methyl, $R^2$ is hydrogen and $R^3$ is hydrogen or methyl, and $R^4$ is selected from $C_3$-$C_5$ alkyl (including $C_3$ alkyl and $C_4$ alkyl, such as propyl, isopropyl, butyl, isobutyl, tert-butyl), and $C_2$-$C_4$ alkoxy (including $C_2$ alkoxy and $C_3$ alkoxy, e.g., ethoxy, propoxy, isopropoxy, butoxy, isobutoxy).

Further, non-limiting examples are compounds of formula (I) wherein $R^1$ is methyl, one of $R^2$, $R^3$ is hydrogen and the other is methyl, and $R^4$ is selected from $C_3$-$C_5$ alkyl (including $C_3$ alkyl and $C_4$ alkyl, such as propyl, isopropyl, butyl, isobutyl, tert-butyl), and $C_2$-$C_4$ alkoxy (including $C_2$ alkoxy and $C_3$ alkoxy, e.g., ethoxy, propoxy, isopropoxy, butoxy, isobutoxy).

Further, non-limiting examples are compounds of formula (I) wherein $R^3$ is methyl, $R^1$ and $R^2$ are hydrogen, and $R^4$ is selected from $C_3$-$C_5$ alkyl (including $C_3$ alky and $C_4$ alkyl, such as propyl, isopropyl, butyl, isobutyl, tert-butyl), and $C_2$-$C_4$ alkoxy (including $C_2$ alkoxy and $C_3$ alkoxy, e.g., ethoxy, propoxy, isopropoxy, butoxy, isobutoxy).

Further, non-limiting examples are compounds of formula (I) wherein $R^1$ is methyl, $R^2$ and $R^3$ are hydrogen, and $R^4$ is selected $C_2$-$C_4$ alkoxy (including $C_2$ alkoxy and $C_3$ alkoxy, e.g., ethoxy, propoxy, isopropoxy, butoxy, isobutoxy) and $C_3$-$C_5$ cycloalkyl (e.g., cyclopropyl, or cyclopentyl).

Further, non-limiting examples are compounds of formula (I) wherein $R^1$ is methyl, $R^2$ and $R^3$ are hydrogen, and $R^4$ is selected from $C_3$-$C_5$ alkyl (including $C_3$ alkyl and $C_4$ alkyl, such as propyl, isopropyl, butyl, isobutyl, tert-butyl), and $C_3$-$C_5$ cycloalkyl (e.g., cyclopropyl, or cyclopentyl).

Further, non-limiting examples are compounds of formula (I) wherein $R^1$ is methyl, $R^2$ and $R^3$ are hydrogen, and $R^4$ is selected from $C_3$-$C_5$ alkyl (including $C_3$ alkyl and $C_4$ alkyl, such as propyl, isopropyl, butyl, isobutyl, tert-butyl.

Further, non-limiting examples are compounds of formula (I) selected from
3-methyl-6-propyl-2,3-dihydro-1H-inden-1-one;
6-isobutyl-2,3-dihydro-1H-inden-1-one;
6-isopropyl-2-methyl-2,3-dihydro-1H-inden-1-one;
6-(tert-butyl)-2-methyl-2,3-dihydro-1H-inden-1-one;
2,3-dimethyl-6-propyl-2,3-dihydro-1H-inden-1-one;
2-methyl-6-propyl-2,3-dihydro-1H-inden-1-one;
6-isobutyl-3-methyl-2,3-dihydro-1H-inden-1-one;
6-isobutyl-2,2-dimethyl-2,3-dihydro-1H-inden-1-one;
6-(tert-butyl)-3-methyl-2,3-dihydro-1H-inden-1-one;
6-cyclopropyl-2-methy 2,3-dihydro-1H-inden-1-one;
6-cyclopentyl-2-methyl-2,3-dihydro-1H-inden-1-one;
2-ethyl-6-isobutyl-2,3-dihydro-1H-inden-1-one;
6-ethyl-2-methyl-2,3-dihydro-1H-inden-1-one;
6-isopentyl-2-methyl-2,3-dihydro-1H-inden-1-one;
6-ethoxy-2-methyl-2,3-dihydro-1H-inden-1-one;
6-isopropoxy-2-methyl-2,3-dihydro-1H-inden-1-one;
2-methyl-6-propoxy-2,3-dihydro-1H-inden-1-one;
6-isobutoxy-2-methyl-2,3-dihydro-1H-inden-1-one;
4-isobutyl-6a-methyl-1a,6a-dihydrocyclopropa[a]inden-6 (1H)-one;
2-methyl(2-methylallyl)-2,3-dihydro-1H-inden-1-one; and
6-butyl-2-methyl-2,3-dihydro-1H-inden-1-one.

The compound of formula (I) may be used alone, as stereoisomeric mixture, or in combination with known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

As used herein, "carrier material" means a material which is practically neutral from a odorant point of view, i.e. a material that does not significantly alter the organoleptic properties of odorants.

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same. It might also be an ingredient that provides additional benefits such as imparting color or texture. It might also be an ingredient that imparts light resistance or chemical stability to one or more ingredients contained in a fragrance composition. A detailed description of the nature and type of adjuvants commonly used in fragrance compositions containing same cannot be exhaustive, but it has to be mentioned that said ingredients are well known to a person skilled in the an.

As used herein, 'fragrance composition' means any composition comprising the compound of formula (I) and a base material, e.g. a diluent conventionally used in conjunction with odorants, such as diethyl phthalate (DEP), dipropylene glycol (DPG), isopropyl myristate (IPM), triethyl citrate (TEC) and alcohol (e.g. ethanol). Optionally, the composition may comprise an anti-oxidant adjuvant. Said anti-oxidant may be selected from Tinogard® TT (BASF), Tinogard® Q (BASF), Tocopherol (including its isomers. CAS 59-02-9; 364-49-8; 18920-62-2; 121854-78-2), 2,6-bis (1,1-dimethylethyl)-4-methylphenol (BHT, CAS 128-37-0) and related phenols, hydroquinones (CAS 121-31-9).

The following list comprises examples of known odorant molecules, which may be combined with the compound of the present invention:

essential oils and extracts, e.g. castoreum, costus root oil, oak moss absolute, geranium oil, tree moss absolute, basil off, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-yang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet® ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol® (3,7-dimethyloct-6-en-ol); Sandalore™ (3-methyl-5-(2,2,3-trimethylcyclopent-3-en-1-yl)pentan-2-ol); terpineol (2-(4-methylcyclohex-3-en-1-yl) propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5'-[1,3]dioxane]);

esters and lactones, e.g. benzyl acetate; cedry acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

The compound according to formula (I) may be used in a broad range of fragranced articles, e.g. in any field of fine and functional perfumery, such as perfumes, air care products, household products, laundry products, body care products and cosmetics. The compound can be employed in widely varying amounts, depending upon the specific article and on the nature and quantity of other odorant ingredients. The proportion is typically from 0.0001 to 30 weight percent of the article. In one embodiment, the compound of the present invention may be employed in a fabric softener in an amount from 0.001 to 0.3 weight percent (e.g. 0.01 to 0.1 including 0.05 weight %). In another embodiment, the compound of the present invention may be used in fine perfumery in amounts from 0.01 to 30 weight percent (e.g. up to about 10 or up to 20 weight percent), more preferably between 0.01 and 5 weight percent. However, these values are given only by way of example, since the experienced perfumer may also achieve effects or may create novel accords with lower or higher concentrations.

In one embodiment there is provided a fragranced article comprising an acceptable amount of at least one compound of formula (I), or a mixture thereof. For example, the fragrance article may comprise 0.000001 weight % to 90 weight % (including 0.00001 weight %, 0.0001 weight %, 0.001 weight %, 0.01 weight %, 0.05 weight %, 0.1 weight %, 0.5 weight %, 1 weight %, 5 weight %, 8 weight %, 10 weight %, 15 weight %, 20 weight %, 25 weight %, 30 weight %, 50 weight %, 60 weight %, 65 weight %) based on the total amount of the article.

The compound as described hereinabove may be employed in a consumer product base simply by directly mixing the compound of formula (I), or a fragrance composition comprising the compound of formula (I), or a mixture thereof, with the consumer product base, or it may, in an earlier step be entrapped with an entrapment material, for example, polymers, capsules, microcapsules and nanocapsules, liposomes, film formers, absorbents such as carbon or zeolites, cyclic oligosaccharides and mixtures thereof, or it may be chemically bonded to substrates, which are adapted to release the fragrance molecule upon application of an external stimulus such as light, enzyme, oxygen, or the like, and then mixed with the consumer product base.

Thus, the invention additionally provides a method of manufacturing a fragranced article, comprising the incorporation of a compound of formula (I), as a fragrance ingredient either by directly admixing the compound to the consumer product base or by admixing a fragrance composition comprising the compound of formula (I), which may then be mixed with a consume product base, using conventional techniques and methods. Through the addition of an olfactory acceptable amount of the compound of the present invention as hereinabove described the odor notes of a consumer product base will be improved, enhanced, or modified.

Thus, the invention furthermore provides a method for improving, enhancing or modifying a consumer product base by means of the addition thereto of an olfactorily acceptable amount of the compound of formula (I).

The invention also provides a fragranced article comprising:

a) as odorant the compound of formula (I), or a mixture thereof; and b) a consumer product base.

As used herein, 'consumer product base' means a composition for use as a consumer product to fulfill specific actions, such as cleaning, softening, and caring or the like. Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, *eucalyptus* oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants.

Cosmetic products include:

(a) cosmetic skincare products, especially both products, skin washing and cleansing products, skincare products, eye makeup, lip care products, nail care products, intimate care products, foot care products;

(b) cosmetic products with specific effects, especially sunscreens, tanning products, de-pigmenting products, deodorants, antiperspirants, hair removers, and shaving products;

(c) cosmetic dental-care products, especially dental and oral care products, tooth care products, cleaners for dental prostheses, adhesives for dental prostheses; and (d) cosmetic hair care products, especially hair shampoos, hair care products, hair setting products hair-shaping products, and hair coloring products.

This list of products is given by way of illustration, and is not to be regarded as being in any way limiting.

Whereas some compounds falling under the general formula (I) as hereinabove defined have been described in the literature, to others only a CAS number is allocated but no publication defining it. Chemical structures to which only a CA number is allocated are, for example, CAS 1518118-62-1, or CAS 1337850-11-9. The compounds disclosed in literature are used as intermediates, e.g. the preparation of catalysts. For example, 6-isopropyl-2-methylindan-1-one (i.e. a compound of formula (I) wherein $R^1$ is methyl $R^2$ and $R^3$ are hydrogen and $R^4$ is isopropyl) which is described in WO 2014/096282, or 6-tert-butyl-2-methylindan-1-one (EP 0 582 194). However, the prior art remains silent with regard to any organoleptic properties. According to our best knowledge most compounds falling under the general formula (I) as hereinabove defined have not been described in literature, and are thus novel in their own right.

Thus, in another aspect of the invention, there is provided a compound of formula (I)

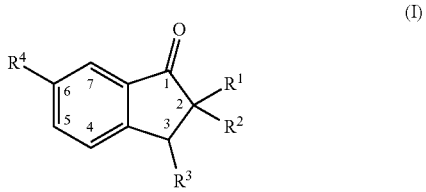

(I)

wherein $R^1$ is selected from methyl and ethyl;

$R^2$ is hydrogen and $R^2$ is hydrogen; or $R^2$ and $R^3$ form together with the carbon atoms to which they are attached $C_3$-$C_5$ cycloalkyl (e.g., cyclobutyl); and $R^4$ is selected from $C_3$-$C_5$ alkyl (including $C_4$ alkyl, such as propyl, isopropyl, butyl, isobutyl, tert-butyl, sec-butyl), $C_2$-$C_5$ alkenyl (such as allyl, methylallyl), $C_3$-$C_4$ alkoxy (e.g. propoxy, isopropoxy, butoxy, isobutoxy), $C_3$-$C_5$ cycloalkyl (e.g., cyclopropyl, cyclopentyl), and $C_3$-$C_6$ cycloakenyl (e.g. cyclopentenyl, cyclobutenyl); with the proviso that $R^4$ is not isopropyl or tert-butyl. Further, non-limiting examples are 3-methyl-6-propyl-2,3-dihydro-1H-inden-1-one, 6-isobutyl-2,3-dihydro-1H-inden-1-one, 2,3-dimethyl-6-propyl-2,3-dihydro-1H-inden-1-one, 6-isobutyl-3-methyl-2,3-dihydro-1H-inden-1-one, 6-isobutyl-2,2-dimethyl-2,3-dihydro-1H-inden-1-one, and 4-isobutyl-5a-methyl-1a,6a-dihydrocyclopropa[a]inden-6(1H)-one.

The compounds of the formula (I) may, for example, be prepared by intramolecular Friedel-Craft acylation of the respective 3-phenylpropanoic acid assisted by Brönsted acid or its acid chloride assisted by a Lewis acid.

Alternatively, compounds of formula (I) wherein $R^4$ is alkyl may be prepared by palladium-catalyzed Suzuki coupling of the respective 6-bromo-indanones with alkyl or cycloalkyl boronic acids. Compounds of formula (I) wherein $R^4$ is alkenyl may be prepared by palladium-catalyzed allylation of the respective 6-bromo-indanones with homoallyl alcohols via retro-allylation. And compounds of formula (I) wherein $R^4$ is alkoxy may be prepared by alkylation of the respective 6-hydroxy-indanones with alky halides.

The invention is now further described with reference to the following non-limiting examples. These examples are for the purpose of illustration only and it is understood that variations and modifications can be made by one skilled in the art.

All products were purified after work-up by either flash chromatography (FC) using Tsingdao Haiyang Chemical silica gel (200±300 mesh) and silica gel Merck grade (60 Å) or distillation. Unless otherwise noted, a mixture of iso-hexane:MTBE (10:1) was used as eluent. NMR spectra were measured in $CDCl_3$ and are reported relative to TMS ($^1H$ NMR spectrum) or relative to $CDCl_3$ ($^{13}C$ NMR spectrum) as follows: chemical shifts (δ ppm), coupling constants J in Hz. GC-MS analysises were run on a MSD5975 mass spectrometer and are reported as m/z list (relative intensity). Odor description refers to the odor of the isomeric mixture of the compounds unless otherwise indicated.

EXAMPLE 1:
6-ISOBUTYL-2-METHYL-2,3-DIHYDRO-1H-INDEN-1-ONE

Procedure A:

To a 100 mL three-necked flask with a magnetic stirrer under argon atmosphere was added phosphonic acid (85% aqueous solution, 31.6 g, 0.274 mol), Phosphorus pentoxide (20.0 g, 0.141 mol) in small portions over 30 min. The mixture was heated to 180° C. and stirred for 30 min before cooled to 80° C. Then 3-(4-isobutylphenyl)-2-methylpropanoic acid (8.00 g, 0.0363 mol) was added and then stirred for 30 min at 80° C. The reaction mixture was cooled to room temperature and poured into 500 mL ice-water with vigorous stirring. The reaction was extracted MTBE (100 mL×2). The combined organic layer was washed successively with water (100 mL×5), saturated aqueous solution of sodium bicarbonate (30.0 mL) and brine (30.0 mL). The organic layer was dried over anhydrous magnesium sulfate. The solvent was removed by rotary evaporation and the crude product was purified by flash chromatography (iso-Hexane/MTBE=20/1) followed by distillation through Kugelrohr (140° C./0.1 mbar) to give 8-isobutyl-2-methyl-2,3-dihydro-1H-inden-1-one (3.93 g, 19.4 mmol, 49% yield) as a colorless liquid.

Procedure B:

To a 500 mL three-necked flask with a magnetic stirrer under argon atmosphere was added 3-(4-isobutylphenyl)-2-methylpropanoic acid (50.0 g, 0.227 mol) in dichloromethane (200 mL). The reaction was cooled to 0° C. $SOCl_2$ (24.8 mL, 340 mmol) was added dropwise over 20 min. The reaction was heated and refluxed for 2 h. The reaction mixture was cooed to room temperature. Solvent and excessive $SOCl_2$ was removed through rotary evaporator to give the crude acid chloride which was dissolved in dichloromethane (50 mL) and used in next step without further purification. To another 500 mL three-necked flask with a magnetic stirrer under argon atmosphere was added aluminum trichloride (33.3 g, 250 mmol) in dichloromethane (300 mL). The reaction was cooled to 0° C. The acid chloride solution in dichloromethane above was added dropwise over 30 min. After completion of the addition, the reaction mixture was stirred overnight at room temperature. The reaction was poured into 500 mL ice-water with vigorous stirring. The reaction was extracted with dichloromethane (100 mL×2). The combined organic layer was washed successively with water (150 mL×2), saturated aqueous solution of sodium bicarbonate (100 mL) and brine (50 mL). The organic layer was dried over anhydrous magnesium sulfate. The solvent was removed by rotary evaporation and the crude product was purified by flash chromatography (iso-Hexane/MTBE=20/1) followed by distillation through Kugelrohr (140° C./0.1 mbar) to give 6-isobutyl-2-methyl-2,3-dihydro-1H-inden-1-one (39.0 g, 193 moil, 85% yield) as a colorless liquid.

Procedure C:

In a 100 mL three-necked round-bottomed flask equipped with a condenser and a dropping funnel was added 6-bromo-2-methyl-2,3-dihydro-1H-inden-1-one (0.300 g, 1.33 mmol), isobutylboronic acid (0.272 g, 2.67 mmol), potassium carbonate (0.553 g, 4.00 mmol) and toluene (20 mL) under argon atmosphere. The result solution was stirred and a mixture of palladium (II) acetate (0.015 g, 0.067 mmol) and 1,3-bis(diphenylphosphino) propane (dppp, 0.033 g, 0.080 mmol) in toluene (8 mL) was added. After addition, the reaction solution was heated to reflux for 2 h. The conversion of the reaction was monitored by GC analysis.

After completion of the reaction, the mixture was cooled to 10° C. and the reaction solution was poured into water (30 mL). The organic phase was separated and the aqueous layer was extracted with MTBE (30 mL×2). The combined organic layers was washed with brine (20 mL), dried (MgSO$_4$), and evaporated in vacuo. The crude oil was purified by silica gel chromatography (iso-Hexane/MTBE=50/1) to give 6-isobutyl-2-methyl-2,3-dihydro-1H-inden-1-one (0.189 g, 70% yield) as a colorless liquid.

$^1$H NMR (300 MHz, CDCl$_3$): δ=7.53 (s, 1H), 7.27-7.40 (m, 2H), 3.36 (dd, J=18.0, 9.0 Hz, 1H), 2.65-2.74 (m, 2H), 2.52 (d, J=7.2 Hz, 2H), 1.83-1.92 (m, 1H), 1.31 (d, J=7.2 Hz, 3H), 0.90 (d, J=6.6 Hz, 6H) ppm; $^{13}$C NMR (75 MHz, CDCl$_3$): δ=209.7 (s), 151.1 (s), 141.1 (s), 136.4 (s), 136.0 (d), 126.1 (d), 124.0 (d), 44.9 (t), 42.3 (d), 34.6 (t), 30.2 (q), 22.2×2 (q), 16.3 (q) ppm; GC/MS (EI): m/z (%): 202 (55) [M$^+$], 187 (11), 159 (100), 145 (29), 131 (23), 91 (14) 77 (6).

Odor description: floral fruity fatty, creamy lactonic like, nectaryl-like, rosy, rose petal, green rose oxide-like.

EXAMPLE 2: 3-METHYL-6-PROPYL-2,3-DIHYDRO-1H-INDEN-1-ONE

The title compound was prepared, following the general procedure A as described in Example 1. Starting from 3-(4-propylphenyl)butanoic acid (5.28 g, 25.6 mml) followed m by distillation through Kugelrohr (140° C./0.10 mbar) to give 3-methyl-6-propyl-2,3-dihydro-1H-inden-1-one as a colorless oil (2.50 g, 61% yield).

Odor description: green, floral, minty, jasmone, jasmine, camonal.

$^1$H NMR (300 MHz, CDCl$_3$): δ=7.54 (s, 1H), 7.39-7.46 (m, 2H), 3.37-3.43 (m, 1H), 2.94 (dd, J=18.9, 72 Hz, 1H), 2.64 (t, J=7.6 Hz, 2H), 2.27 (dd, J=18.9, 3.3 Hz, 1H), 1.59-1.72 (m, 2H), 1.39 (d, J=72 Hz, 3H), 0.93 (f, J=7.2 Hz, 3H) ppm; $^{13}$C NMR (75 MHz, CDCl$_6$): δ=206.6 (s), 157.7 (s), 142.2 (s), 136.6 (s), 135.6 (d), 125.0 (d), 122.8 (d), 45.7 (t), 37.5 (t), 32.5 (d), 24.4 (t), 21.4 (q), 13.7 (q) ppm; GC/MS (EI): m/z (%): 188 (70) [M$^+$], 173 (73), 159 (100), 145 (20), 131 (31), 115 (28), 91 (12).

EXAMPLE 3: 6-ISOBUTYL-2,3-DIHYDRO-1H-INDEN-1-ONE

The title compound was prepared, following the general procedure A as described in Example 1. Starting from of 3-(4-isobutylphenyl)propanoic acid (45.0 g, 218 mmol) followed by distillation through Kugelrohr (140° C./0.14 mbar) to give 6-isobutyl-2,3-dihydro-1H-inden-1-one as a colorless oil (22.0 g, 54% yield).

Odor description: green floral, isobutyl benzoate.

$^1$H NMR (300 MHz, CDCl$_3$): δ=7.53 (s, 1H), 7.35-7.41 (m, 2H), 3.10 (t, J=6.0 Hz, 2H), 2.70 (t, J=6.0 Hz, 2H), 2.53 (d, J=7.2 Hz, 2H), 1.80-1.92 (m, 1H), 0.90 (d, J=6.6 Hz, 6H) ppm; $^{13}$C NMR (75 MHz, CDCl$_3$): δ=207.3 (s), 152.9 (s), 141.1 (s), 137.1 (s), 135.9 (d), 126.2 (d), 123.7 (d), 44.9 (t), 36.6 (t), 30.2 (d), 25.4 (t), 22.2×2 (q) ppm: GC/MS (EI): m/z (%): 188 (60) [M$^+$], 173 (1), 146 (100), 115 (34), 104 (26), 91 (16), 77 (5).

EXAMPLE 4: 6-ISOPROPYL-2-METHYL-2,3-DIHYDRO-1H-INDEN-1-ONE

The title compound was prepared, following the general procedure A as described in Example 1. Starting from of 3-(4-isopropylphenyl)-2-methylpropanoic acid (10.0 g, 48.5 mmol) followed by distillation through Kugelrohr (140° C./0.10 mbar) to give 6-isopropyl-2-methyl-2,3-dihydro-1H-inden-1-one as a colorless oil (6.80 g, 74% yield).

Odor description: green fatty, lactonic fruity, rosy metallic.

$^1$H NMR (300 MHz, CDCl$_6$): δ=7.63 (s, 1H), 7.46-7.49 (m, 1H), 7.37 (d, J=7.8 Hz 1H), 3.32-4.40 (m, 1H), 2.93-4.02 (m, 1H), 2.65-2.75 (m, 2H), 1.31 (d, J=7.2 Hz, 3H), 1.27 (d, J=8.9 Hz, 6H) ppm; $^{13}$C NMR (75 MHz, CDCl$_6$): δ=209.7 (s), 151.3 (s), 148.5 (s), 136.5 (s), 133.8 (d), 126.4 (d), 121.2 (d), 42.4 (d), 34.6 (t), 33.9 (d), 24.0×2 (q), 16.4 (q) ppm; GC/MS (EI): m/z (%): 188 (43) [M$^+$], 173 (100), 145 (17), 117 (26), 91 (10), 77 (4)

EXAMPLE 5: 6-(TERT-BUTYL)-2-METHYL-2,3-DIHYDRO-1H-INDEN-1-ONE

The title compound was prepared, following the general procedure A as described in Example 1. Starting from 3-(4-(tert-butyl)phenyl)-2-methylpropenoic acid (10.0 g, 45.4 mmol) followed by distillation through Kugelrohr (140° C./0.14 mbar) to give 6-(tert-butyl)-methyl-2,3-dihydro-1H-inden-1-one as a colorless oil (7.50 g, 82% yield).

Odor description: green fatty, lactonic fruity, slightly fatty cinnamic.

$^1$H NMR (300 MHz, CDCl$_3$): δ=7.78 (s, 1H), 7.65-7.68 (m, 1H), 7.39 (d, J=7.8 Hz, 1H), 3.32-3.40 (m, 1H), 2.65-2.75 (m, 2H), 1.34 (s, 9H), 1.31 (d, J=7.5 Hz, 3H) ppm, $^{13}$C NMR (75 MHz, CDCl$_3$): δ=209.8 (s), 150.9 (s), 150.9 (s), 136.3 (s), 132.5 (d), 126.1 (d), 120.3 (d), 42.4 (d), 34.8 (s), 34.5 (t), 31.4×3 (q), 16.4 (q) ppm; GC/MS (EI): m/z (%): 202 (23) [M$^+$], 187 (100), 159 (15), 131 (19), 115 (10), 91 (6), 77 (2).

EXAMPLE 6: 2,3-DIMETHYL-6-PROPYL-2,3-DIHYDRO-1H-INDEN-1-ONE

The title compound was prepared, following the general procedure A as described in Example 1. Starting from 2-methyl-3-(4-propylphenyl)butanoic acid (8.00 g, 36.3 mmol) followed by distillation through Kugelrohr (140° C./0.10 mbar) to give 2,3-dimethyl-6-propyl-2,3-dihydro-1H-inden-1-one as a colorless oil (1.50 g, 20% yield).

Odor description: green fatty oily, fatty fruity lactonic, metallic rosy.

$^1$H NMR (300 MHz, CDCl$_3$): δ=7.54 (s, 1H), 7.28-7.486 (m, 2H), 2.85-2.94 (m, 1H), 2.64 (t, J=7.5 Hz, 2H), 2.19-2.74 (m, 1H), 1.59-1.71 (m, 2H), 1.44 (d, J=7.2 Hz, 3H), 1.31 (d, J=7.5 Hz, 3H), 0.94 (t, J=7.5 Hz, 3H) ppm; $^{13}$C NMR (75 MHz, CDCl$_3$): δ=208.6 (s), 155.5 (s), 142.2 (s), 136.0 (s), 135.5 (d), 124.6 (d), 122.9 (d), 51.8 (d), 41.4 (d), 37.6 (t), 24.5 (t), 19.2 (q), 14.2 (q) 13.7 (q) ppm; GC/MS (EI): m/z (%): 202 (40) [M$^+$], 187 (100), 173 (24), 145 (14), 115 (15), 91(8), 77 (3).

EXAMPLE 7: 2-METHYL-6-PROPYL-2,3-DIHYDRO-1H-INDEN-1-ONE

The title compound was prepared, following the general procedure A as described in Example 1. Starting from 2-methyl-3-(4-propylphenyl)propanoic acid (6.00 g, 29.1 mmol) followed by distillation through Kugelrohr (160° C./0.20 mbar) to give 2-methyl-6-propyl-2,3-dihydro-1H-inden-1-one as a colorless oil (3.50 g, 64% yield).

Odor description: green, floral, fatty, rosy cinnamic.

$^1$H NMR (300 MHz, CDCl$_3$): δ=7.57 (s, 1H) 7.34-7.43 (m, 2H), 3.36 (dd, J=18.0, 9.0 Hz, 1H), 2.81-2.74 (m, 4H), 1.69-1.71 (m, 2H), 1.30 (d, J=7.2 Hz, 3H), 0.93 (t, J=7.2 Hz, 3H) ppm; $^{13}$C NMR (75 MHz, CDCl$_3$): δ=209.7 (s), 151.1 (s), 142.1 (s), 136.5 (s), 135.5 (d), 126.2 (d), 123.3 (d), 42.3 (d), 37.8 (t), 34.6 (t), 24.5 (t), 16.3 (q), 13.7 (q) ppm; GC/MS (EI): m/z (%): 188 (62) [M$^+$], 173 (70) 159 (100), 145 (19), 131 (31), 91 (16), 77 (7).

EXAMPLE 8:
6-ISOBUTYL-3-METHYL-2,3-DIHYDRO-1H-INDEN-1-ONE

The title compound was prepared, following the general procedure B as described in Example 1. Starting from 3-(4-isobutylphenyl)butanoic acid (25.0 g, 113 mmol) followed by distillation through Kugelrohr (150° C./0.10 mbar) to give 6-isobutyl-3-methyl-2,3-dihydro-1H-inden-1-one as a colorless oil (15.0 g, 65% yield).

Odor description: green rosy, fatty, metallic rosy, fatty fruity floral.

$^1$H NMR (300 MHz, CDCl$_3$) δ=7.50 (s, 1H), 7.41 (s, 2H), 3.37-3.43 (m, 1H), 2.93 (dd, J=19.2, 7.5 Hz, 1H), 2.53 (d, J=7.2 Hz, 2H), 2.27 (dd, J=18.9, 27 Hz, 1H), 1.80-1.94 (m, 1H), 1.39 (d, J=72 Hz, 3H), 0.90 (d, J=6.6 Hz, 6H) ppm; $^{13}$C NMR (75 MHz, CDCl$_3$): δ=206.7 (s), 157.7 (s), 141.2 (s), 136.4 (s), 136.1 (d), 124.9 (d), 123.4 (d), 45.7 (t), 44.9 (t), 32.5 (d), 30.2 (d), 222×2 (q), 21.4 (q) ppm; GC/MS (EI): m/z (%): 202 (65) [M$^+$], 187 (11), 159 (100), 145 (27), 131 (22), 115 (29), 91 (13), 77 (4).

EXAMPLE 9:
6-ISOBUTYL-2,2-DIMETHYL-2,3-DIHYDRO-1H-INDEN-1-ONE

The title compound was prepared, following the general procedure A as described in Example 1. Starting from 3-(4-isobutylphenyl)-2,2-dimethylpropanoic acid (5.36 g, 22.9 mmol) followed by distillation through Kugeltrohr (150° C./0.10 mbar) to give 6-isobutyl-2,2-dimethyl-2,3-dihydro-1H-inden-1-one as a colorless oil (3.50 g, 71% yield).

Odor description: floral fatty, fruity, green, rubbery, muguet.

$^1$H NMR (300 MHz, CDCl$_3$): δ=7.54 (s, 1H), 7.31-7.40 (m, 2H), 2.96 (s, 2H), 2.52 (d, J=7.2 Hz, 2H), 1.83-1.92 (m, 1H), 1.23 (s, 6H), 0.90 (d, J=6.6 Hz, H) ppm; $^{13}$C NMR (75 MHz, CDCl$_3$): δ=211.6 (s), 149.8 (s), 141.2 (s), 136.2 (d), 135.3 (s), 126.2 (d), 124.4 (d), 45.8 (s), 45.0 (t), 42.5 (t), 30.2 (d), 253×2 (q), 22.3×2 (q) ppm; GC/MS (EI): m/z (%): 216 (59) [M$^+$], 201 (100), 173 (87), 159 (21), 115 (17).

EXAMPLE 10: 6-(TERT-BUTYL)-3-METHYL-2,3-DIHYDRO-1H-INDEN-1-ONE

The title compound was prepared, following the general procedure B as described in Example 1. Starting from 3-(4-(tert-buty)phenyl)butanoic acid (4.43 g, 20.1 mmol) followed by distillation through Kugelrohr (150° C./0.10 mbar) to give 6-(tert-buty)-3-methyl-2,3-dihydro-1H-inden-1-one as a colorless oil (2.60 g, 64% yield).

Odor description: fruity, floral.

$^1$H NMR (300 MHz, CDCl$_3$): δ=7.75 (d, J=1.8 Hz, 1H), 7.68 (dd, J=8.1, 1.8 Hz, 1H), 7.44 (d, J=8.1 Hz, 1H), 3.36-3.42 (m, 1H), 2.93 (dd, J=18.9, 7.5 Hz, 1H), 2.26 (dd, J=18.9, 3.3 Hz, 1H), 1.39 (d, J=6.6 Hz, 3H), 1.34 (s, 9H) ppm; $^{13}$C NMR (75 MHz, CDCl$_3$): δ=206.6 (s), 157.4 (s), 150.8 (s), 136.3 (s), 132.5 (d), 124.9 (d) 119.6 (d), 46.7 (t), 34.7 (t), 32.3 (d), 31.3×3 (q), 21.3 (q) ppm; GC/MS (EI): m/z (%): 202 (22) [M$^+$], 187 (100), 159 (19), 145 (21), 91 (6), 77 (4).

EXAMPLE 11:
6-CYCLOPROPYL-2-METHYL-2,3-DIHYDRO-1H-INDEN-1-ONE

The title compound was prepared, following the general procedure C as described in Example 1. 6-Bromo-2-methyl-2,3-dihydro-1H-inden-1-one (1.50 g, 6.66 mmol), cyclopropylboronic acid (1.15 g, 13.33 mmol), potassium carbonate (2.76 g, 20.0 mmol), palladium (II) acetate (0.075 g, 0.333 mmol) and 1,1-bis(diphenyphosphino)ferrocene (dppf ligand; 0.222 g, 0.400 mmol) in toluene (30 mL) were reacted at reflux under argon atmosphere for 2 h followed by distillation through Kugelrohr (135° C./0.10 mbar) to give 6-cyclopropyl-2-methyl-2,3-dihydro-1H-inden-1-one as a colorless liquid (1.00 g, 81% yield).

Odor description: green, fatty, floral, rosy metallic.

$^1$H NMR (300 MHz, CDCl$_3$): δ=7.39 (s, 1H), 7.29-7.36 (m, 2H), 3.33 (dd, J=17.7, 5.7 Hz, 1H) 2.61-2.71 (m, 2H), 1.88-1.97 (m, 1H), 1.28 (d, J=7.2 Hz, 3H), 0.95-1.01 (m, 2H), 0.68-0.73 (m, 2H) ppm; $^{13}$C NMR (75 MHz, CDCl$_3$) δ=209.5 (s), 150.8 (s), 143.7 (s), 136.4 (s), 133.2 (d), 1262 (d), 119.9 (d), 42.3 (d), 34.5 (t), 16.3 (q), 15.1 (d), 9.5×2 (t) ppm; GC/MS (EI): m/z (%): 186 (72) [M$^+$], 171 (100), 158 (16), 143 (30), 128 (42), 115 (45), 91 (10).

EXAMPLE 12:
6-CYCLOPENTYL-2-METHYL-2,3-DIHYDRO-1H-INDEN-1-ONE

The title compound was prepared, following the general procedure C as described in Example 1. 68-Bromo-2-methyl-2,3-dihydro-1H-inden-1-one (2.00 g, 8.89 mmol), cyclopentylboronic acid (2.03 g, 17.8 mmol), potassium carbonate (3.68 g, 25.7 mmol), palladium (II) acetate (0.080 g, 0,355 mmol) and 1,1'-bis(diphenylphosphino)ferrocene (dppf ligand: 0.246 g, 0.444 mmol) in toluene (20 ml) were reacted at reflux under argon atmosphere for 2 h followed by distillation through Kugelrohr (140° C./0.15 mbar) to give 6-cyclopentyl-2-methyl-2,3-dihydro-1H-inden-1-one as a colorless liquid (0.50 g, 26% yield).

Odor description: fruity fatty floral, peachy, green rosy.

$^1$H NMR (300 MHz, CDCl$_3$): δ=7.63 (s, 1H), 7.48 (d, J=7.8 Hz, 1H), 7.35 (d, J=7.8 Hz, 1H), 3.35 (dd, J=18.0, 9.0 Hz, 1H), 2.98-3.10 (m, 1H), 2.64-2.73 (m, 2H), 2.07-2.09 (m, 2H), 1.58-1.81 (m, 6H), 1.30 (d, J=7.5 Hz, 3H) ppm; $^{13}$C NMR (75 MHz, CDCl$_3$): δ=209.7 (s), 151.2 (s), 148.2 (s), 136.4 (s), 134.4 (d), 126.2 (d), 121.8 (d), 45.8 (d), 42.4 (d), 34.7×2 (t), 34.6 (t), 25.5×2 (t), 18.4 (q) ppm; GC/MS (EI): m/z (%): 214 (100) [M$^+$], 199 (55), 186 (39), 172 (61), 157 (47), 143 (32), 129 (59)<115 (40).

EXAMPLE 13:
2-ETHYL-6-ISOBUTYL-2,3-DIHYDRO-1H-INDEN-1-ONE

To a solution of (E)-2-(4-isobutylbenzylidene)butanal (5.35 g, 24.7 mmol) in toluene (50 mL) was added methanesulfonamide (2.82 g, 29.7 mmol) and iron(III) chloride (0.80 g, 4.9 mmol). The mixture was stirred and heated to 65'C for 16 h. After the aldehyde was completely consumed (monitored by GC) the reaction was cooled to room temperature. Then methanol (30 mL) and a solution of sodium hydroxide (2.47 g, 61.8 mmol) in water (20 mL) was added. The mixture was stirred for 2 h at room temperature. The resulting mixture was then treated with methanol (30 ml) and dropwise with 37% hydrogen chloride (626 ml, 74.2 mmol), heated to 70° C. and stirred overnight. After cooling, water (200 ml) was added and the solution was extracted with MTBE (100.3 mL). The combined organic layers were washed with brine, dried with MgSO$_4$, filtered and concentrated to give the crude product. The residue was purified by silica gel chromatography (hexane:MTBE=50:1) followed by distillation through Kugelrohr (160° C./0.15 mbar) to give 2-ethyl-6-isobutyl-2,3-dihydro-1H-inden-1-one as colorless oil (2.60 g, 49% yield).

Odor description: floral fatty green, oily cinnamic, nectaryl $^1$H NMR (300 MHz, CDCl$_3$): δ=7.52 (s, 1H), 7.34-7.40 (m, 2H), 3.28 (dd, J=17.1, 7.8 Hz, 1H), 2.78 (dd, J=17.1, 3.9 Hz, 1H), 2.58-2.65 (m, 1H), 2.52 (d, J J=7.2 Hz, 2H), 1.80-2.04 (m, 2H), 1.46-1.60 (m, 1H), 1.01 (t, J=7.5 Hz, 3H), 0.90 (d, J=6.6 Hz, 6H) ppm: $^{13}$C NMR (75 MHz, CDCl$_3$): δ=209.2 (s), 151.5 (s), 141.1 (s), 137.0 (s), 136.0 (d), 126.1 (d), 123.8 (d), 49.2 (d), 44.9 (t), 32.0 (t), 30.2 (d), 24.5 (t), 22.3×2 (q), 11.7 (q) ppm: GC/MS (EI): m/z (%): 216 (7) [M$^+$], 188 (100), 173 (33), 145 (36), 131 (20), 91 (7), 77 (7).

EXAMPLE 14:
6-ETHYL-2-METHYL-2,3-DIHYDRO-1H-INDEN-1-ONE

The title compound was prepared, following the general procedure described in Example 13, starting from (E)-3-(4-ethylphenyl-2-methylacrylaldehyde (5.0 g, 28.7 mmol), methanesulfonamide (4.09 g, 43.0 mmol) and iron(III) chloride (0.931 g, 5.74 mmol) followed by distillation through Kugelrohr (150° C./0.12 mbar) to give 6-ethyl-2-methyl-2,3-dihydro-1H-inden-1-one as a colorless oil (1.30 g, 26% yield).

Odor description: green minty floral, carvone jasmine fruity.

$^1$H NMR (300 MHz, CDCl$_3$): δ=7.58 (s, 1H), 7.34-7.44 (m, 2H), 3.35 (dd, J=18.0, 8.7 Hz, 1H), 2.65-2.73 (m, 4H), 1.22-1.31 (m, 6H) ppm; $^{13}$C NMR (75 MHz, CDCl$_3$): δ=209.6 (s), 151.1 (s), 143.7 (s), 136.5 (s), 135.0 (d), 126.3 (d), 122.8 (d), 42.3 (d), 34.6 (t), 28.5 (t), 16.3 (q), 15.6 (q) ppm; GC/MS (EI): m/z (%): 174 (60) [M$^+$], 159 (100), 145 (23), 131 (32), 115 (22), 91 (13), 77 (7).

EXAMPLE 15: 6-(SEC-BUTYL)-2-METHYL-2,3-DIHYDRO-1H-INDEN-1-ONE

The title compound was prepared, following the general procedure as described in Example 13. Starting from (E)-3-(4-(sec-buty)phenyl)-2-methylacrylaldehyde (5.00 g, 14.8 mmol), methanesulfonamide (1.89 g, 17.8 mmol) and iron (III) chloride (0.481 g, 2.97 mmol) followed by distillation through Kugelrohr (150° C./0.08 mbar) to give 6-ethyl-2-methyl-2,3-dihydro-1H-inden-1-one as a colorless oil (1.00 g, 33% yield).

Odor description: green rosy metallic, green leathery, fatty floral.

(mixture of two isomers in a ratio of 1:1) $^1$H NMR (300 MHz, CDCl$_3$): δ=7.59 (s, 1H), 7.38-7.44 (m, 2H), 3.32-3.41 (m, 1H), 2.66-2.73 (m, 3H), 1.58-1.63 (m, 2H), 1.31 (d, J=7.2 Hz, 3H), 1.25 (d, J=6.9 Hz, 3H), 0.81 (t, J=7.2 Hz, 3H) ppm; $^{13}$C NMR (75 MHz, CDCl$_3$): δ=209.8 (s), 151.3 (s), 147.2 (s), 138.5 (s), 134.4 (d), 134.3 (d), 126.3 (d), 121.9 (d), 121.9 (d), 42.4 (d), 41.4 (d), 34.6 (t), 31.1 (t), 21.9 (q), 16.3 (q), 12.2 (q) ppm; GC/MS (EI): m/z (%): 202 (30) [M$^+$], 187 (5), 173 (100), 159 (7), 117 (27), 91 (8), 77 (4)

EXAMPLE 16:
6-ISOPENTYL-2-METHYL-2,3-DIHYDRO-1H-INDEN-1-ONE

The title compound was prepared, following the general procedure as described in Example 13. Starting from (E)-3-(4-isopentylphenyl)-2-methylacrylaldehyde (5.00 g, 18.5 mmol), methanesulfonamide (2.11 g, 222 mmol) and iron (III) chloride (0.600 g, 3.70 mmol) followed by distillation through Kugelrohr (162° C./0.10 mbar) to give 6-isopentyl-2-methyl-2,3-dihydro-1H-inden-1-one as a colorless oil (1.30 g, 33% yield).

Odor description: green rosy, fatty lactonic, rosy powdery, cinnamate like.

$^1$H NMR (300 MHz, CDCl$_3$): δ=7.57 (s, 1H), 7.32-7.42 (m, 2H), 3.34 (dd, J=18.0, 8.7 Hz, 1H), 2.62-2.70 (m, 4H), 1.46-1.62 (m, 3H), 1.29 (d, J=7.2 Hz, 3H), 0.93 (d, J=6.9 Hz, 6H) ppm; $^{13}$C NMR (75 MHz, CDCl$_3$): δ=209.5 (s), 151.0 (s), 142.5 (s), 136.5 (s), 135.4 (d), 126.3 (d), 123.1 (d) 42.3 (d), 40.8 (t), 34.6 (t), 33.3 (t), 27.5 (d), 22.5×2 (q), 16.3 (q) ppm; GC/MS (EI): m/z (%): 216 (80) [M$^+$], 201 (30), 187 (1), 159 (98), 132 (100), 118 (55), 104 (55), 91(23), 77 (8).

EXAMPLE 17:
6-ETHOXY-2-METHYL-2,3-DIHYDRO-1H-INDEN-1-ONE

To a solution of 6-hydroxy-2-methyl-2,3-dihydro-1H-inden-1-one (2.00 g, 12.3 mmol) in N,N-Dimethylformamide (30 mL), iodoethane (2.50 g, 16.0 mmol) and potassium carbonate (1.87 g, 13.5 mmol) were added at room temperature. The mixture was heated for 6 h at 55° C. under argon atmosphere. The reaction was cooled to room temperature, quenched with water (60 mL) and extracted with MTE (30 mL×3). The combined organic layer was dried over MgSO$_4$, filtrated end concentrated. The residue was purified by chromatography on silica gel (iso-Hexane/MTBE=9/1) followed by distillation via Kugelrohr (145° C./010 mbar) to give 6-ethoxy-2-methyl-2,3-dihydro-1H-inden-1-one as a white powder (2.00 g, 85% yield).

Odor description: green, waxy fruity, rosy.

$^1$H NMR (300 MHz, CDCl$_3$): δ=7.33 (d, J=9.0 Hz, 1H), 7.16-7.19 (m, 2H), 4.06 (q, J=6.9 Hz, 2H), 3.32 (dd, J=16.5, 7.5 Hz, 1H), 2.70-2.76 (m, 1H), 2.64 (dd, J=16.5, 3.6 Hz, 1H), 1.42 (t, J=6.9 Hz, 3H), 1.31 (d, J=7.5 Hz, 3H) ppm; $^{13}$C NMR (75 MHz, CDCl$_2$): δ=209.5 (s), 158.7 (s), 146.1 (s), 137.4 (s), 127.2 (d), 124.5 (d), 105.8 (d), 63.8 (t), 42.8 (d), 34.3 (t), 16.4 (q), 14.7 (q) ppm; GC/MS (EI): m/z (%): 190 (80) [M$^+$], 175 (35), 162 (16), 147 (100), 133 (35), 119 (11), 105 (10).

EXAMPLE 18: 6-ISOPROPOXY-2-METHYL-2,3-DIHYDRO-1H-INDEN-1-ONE

The title compound was prepared, following the general as described in Example 17. 6-Hydroxy-2-methyl-2,3-dihydro-1H-inden-1-one (1.00 g, 6.17 mmol), 2-bromopropane (3.41 g, 27.7 mmol) and potassium carbonate (2.81 g, 20.3 mmol) in dimethylformamide (DMF; 30 m) were reacted at 55° C. under argon for 6 h to give 6-isopropoxy-2-methyl-2,3-dihydro-1-inden-1-one as a colorless liquid (0.90 g, 72% yield).

Odor description: green rosy fatty floral, slightly fatty fruity, metallic rosy $^1$H NMR (300 MHz, CDCl$_3$): =7.31-7.40 (m, 1H), 7.13-7.18 (m, 2H), 4.58-4.60 (m, 1H), 3.31 (dd, J=16.5, 7.5 Hz, 1H), 2.60-2.76 (m, 2H), 1.34 (d, J=6.0 Hz, 6H), 1.30 (d, J=7.2 Hz, 3H) ppm; $^{13}$C NMR (75 MHz, CDCl$_3$): δ=209.5 (s), 157.6 (s), 145.9 (s), 137.4 (s), 127.3 (d), 125.6 (d), 107.3 (d), 70.2 (d), 42.8 (d), 34.2 (t), 21.9 (q), 21.9 (q), 16.4 (q) ppm; GC/MS (E): m/z (%): 204 (33) [M$^+$], 189 (1), 162 (50), 147 (100), 105 (7), 91 (5), 77 (8)

EXAMPLE 19: 2-METHYL-6-PROPOXY-2,3-DIHYDRO-1H-INDEN-1-ONE

The title compound was prepared, following the general as described in Example 17. 6-Hydroxy-2-methyl-2,3-dihydro-1H-inden-1-one (2.00 g, 12.3 mmol), 1-bromo-2-methylpropane (7.60 g, 55.5 mmol) and potassium carbonate (2.36 g, 17.3 mmol) in acetone (30 mL) were refluxed under argon atmosphere for 6 h to give 2-methyl-6-propoxy-2,3-dihydro-1H-inden-1-one as a white powder (1.30 g, 52% yield).

Odor description: waxy, fatty fruity, green floral.

$^1$H NMR (300 MHz, CDCl$_3$): δ=7.32 (d, J=9.0 Hz, 1H), 7.17-7.20 (m, 2H), 3.94 (t, J=6.3 Hz, 2H), 3.32 (dd, J=16.5, 7.5 Hz, 1H), 2.70-2.78 (m, 1H), 2.84 (dd, J=16.5, 3.9 Hz, 1H), 1.76-1.87 (m, 2H), 1.30 (d, J=7.5 Hz, 3H), 1.04 (t, J=7.6 Hz, 34) ppm; $^{13}$C NMR (75 MHz, CDCl$_3$): δ=209.5 (s), 158.9 (s), 146.0 (s), 137.4 (s), 127.2 (d), 124.5 (d), 105.9 (d), 69.9 (t), 42.8 (d), 34.3 (t), 22.4 (t), 16.4 (q), 10.5 (q) ppm; GC/MS (EI): m/z (%): 204 (52) [M$^+$], 189 (1), 162 (42), 147 (100), 134 (25), 115 (10), 91 (10).

EXAMPLE 20: 6-ISOBUTOXY-2-METHYL-2,3-DIHYDRO-1H-INDEN-1-ONE

The title compound was prepared, following the general as described in Example 17, 6-Hydroxy-2-methyl-2,3-dihydro-1H-inden-1-one (2.00 g, 12.3 mmol), 1-bromo-2-methylpropane (7.60 g, 55.5 mmol) and potassium carbonate (5.62 g, 40.7 mmol) in DMF (30 mL) were reacted at 55° C. under argon atmosphere for 6 h to give 6-isobutoxy-2-methyl-2,3-dihydro-1H-inden-1-one (1.90 g, 71% yield) as a colorless liquid.

Odor description: floral fruity fatty, green anisic.

$^1$H NMR (300 MHz, CDCl$_3$): δ=7.33 (d, J=8.1 Hz, 1H), 7.17-7.21 (m, 2H), 3.75 (d, J=6.6 Hz, 2H), 3.32 (dd, J=16.5, 7.5 Hz, 1H), 2.70-2.79 (m, 1H), 2.64 (dd, J=16.5, 3.6 Hz, 1H), 2.02-2.16 (m, 1H), 1.31 (d, J=7.2 Hz, 3H), 1.02 (d, J=6.6 Hz, 6H) ppm; $^{13}$C NMR (75 MHz, CDCl$_3$): δ=209.5 (s), 159.0 (s), 148.0 (s), 137.4 (s), 127.2 (d), 124.5 (d), 105.9 (d), 74.8 (t), 42.8 (d), 34.3 (t), 28.1 (d), 19.2×2 (q), 16.4 (q) ppm; GC/MS (EI): m/z (%): 218 (41) [M$^+$], 203 (1), 162 (70), 147 (100), 134 (28), 115 (11), 91 (8).

EXAMPLE 21: 4-ISOBUTYL-6A-METHYL-1A,6A-DIHYDROCYCLOPROPA[A]INDEN-6(1H)-ONE

In a 250 mL three-necked round-bottomed flask was added 4-isobutyl-6a-methyl-1,1a,6,6a-tetrahydrocyclopropa[a]inden-6-ol (0.40 g, 1.85 mmol) in dichloromethane (50 mL) to give a colorless solution, pyridinium chlorochromate (1.00 g, 4.62 mmol) was added. The reaction mixture was stirred at room temperature for 2 h until completion of the conversion. The reaction was diluted by iso-hexane (100 ml) and then filtered through a small pad of silica gel. The silica gel was rinsed with dichloromethane and iso-hexane. The combined filtrate was concentrated to give a yellow residue which was further purified by column chromatography (iso-Hexane/MTBE=20/1) to give 4-isobutyl-6a-methyl-1a,6a-dihydrocyclopropa[a]inden-6(1H)-one (60 mg, 15% yield) as a tight yellow liquid.

Odor description: fatty, fruity, green, floral, with some rubbery facets.

$^1$H NMR (300 MHz, CDCl$_3$): δ=7.34 (s, 1H), 7.12-7.21 (m, 2H), 2.58-2.61 (m, 1H), 2.38 (d, J=6.9 Hz, 2H), 1.70-1.79 (m, 1H), 1.44 (s, 3H), 1.29-1.31 (m, 2H), 0.79 (d, J=6.9 Hz, 6H) ppm; $^{13}$C NMR (75 MHz, CDCl$_3$): δ=205.0 (s), 152.2 (s) 140.4 (s), 134.6 (d), 133.6 (s) 125.0 (d), 123.7 (d), 44.9 (t), 39.8 (t), 33.1 (s), 30.2 (d), 28.2 (d) 22.2×2 (q), 13.6 (q) ppm; GC/MS (EI): m/z (%): 214 (37) [M$^+$], 199 (2), 171 (100), 158 (18), 128 (40), 115 (13).

EXAMPLE 22: 2-METHYL-6-(2-METHYLALLYL)-2,3-DIHYDRO-1H-INDEN-1-ONE

Cesium carbonate (3.26 g, 10.0 mmol) was placed in 100 mL three-necked reaction flask equipped with a condenser. Palladium (II) acetate (0.075 g, 0.333 mmol) and triphenylphosphine (0.35 g, 1.33 mmd) were added in the reaction flask. The flask was then filled with argon. Toluene (35 mL), 3-isopropyl-2,5-dimethylhex-5-en-3-ol (1.36 g, 8.00 mmol) and 6-bromo-2-methyl-2,3-dihydro-1H-indenone (1.50 g, 6.66 mmol) were sequentially added at room temperature. The resulting mixture was heated at reflux for 2 h. After the mixture was cooled to room temperature, it was filtered through a short silica gel pad, and washed with MTBE (100 mL). Remove the solvent by rotary evaporate, and the residue was purified by silica gel chromatography (iso-Hexane/MTBE=50/1) to give 2-methyl-6-(2-methylallyl)-2,3-dihydro-1H-inden-1-one (1.20 g, 90% yield) as alight yellow oi.

Odor description: fatty, fruity, green, floral, cinnamic cinnamate like.

$^1$H NMR (300 MHz, CDCl$_3$): δ=7.58 (s, 1H), 7.36-7.45 (m, 2H), 4.83 (s, 1H), 4.74 (s, 1H), 3.36 (s, 2H), 3.32-3.41 (m, 1H), 2.66-2.75 (m, 2), 1.66 (s, 3H), 1.31 (d, J=7.2 Hz, 3H) ppm; $^{13}$C NMR (75 MHz, CDCl$_3$): δ=209.6 (s), 151.6 (s) 144.4 (s), 139.3 (s), 136.6 (s), 135.7 (d), 126.3 (d), 124.0 (d), 112.5 (t), 44.2 (t), 42.4 (d), 34.7 (t), 22.0 (q), 16.3 (q) ppm; GC/MS (EI): m/z (%): 200 (29) [M$^+$], 185 (100), 172 (57), 157 (75), 144 (73), 129 (85), 115 (60).

EXAMPLE 23: 6-BUTYL-2-METHYL-2,3-DIHYDRO-1H-INDEN-1-ONE

The title compound was prepared, following the general procedure C as described in Example 1. 6-Bromo-2-methyl-2,3-dihydro-1H-inden-1-one (4.00 g, 17.8 mmol), butylboronic acid (3.62 g, 35.5 mmol), potassium carbonate (3.68 g, 26.7 mmol), palladium (II) acetate (0.160 g, 0.711 mmol) and 1,1'-bis(diphenylphosphino)ferrocene (dppf ligand; 0.394 g, 0.711 mmol) in toluene (30 mL) were reacted at reflux under argon atmosphere for 2 h followed by distillation through Kugelrohr (145° C./0.10 mbar) to give 6-butyl-2-methyl-2,3-dihydro-1H-inden-1-one as a colorless liquid (0.67 g, 18% yield).

Odor description green fatty floral: rosy, peach, green rubbery slightly leathery isobutyl salicylate $^1$H NMR (300 MHz, CDCl$_3$): δ=7.57 (s, 1H), 7.42 (d, J=7.1 Hz, 1H), 7.35 (d, J=7.1 Hz, 1H), 3.36 (dd, J=18.0, 9.0 Hz, 1H), 2.64-2.74 (m, 4H), 1.56-1.66 (m, 2H), 1.26-1.38 (m, 5H), 0.92 (t, J=7.5 Hz, 3H) ppm. $^{13}$C NMR (75 MHz, CDCl$_3$): δ=209.7 (s), 151.1 (s), 142.4 (s), 136.5 (s), 135.5 (d), 126.2 (d), 123.3 (d), 42.3 (d), 35.2 (t), 34.6 (t), 33.6 (t), 22.2 (t), 16.4 (q), 13.9 (q) ppm; GC/MS (EI): m/z (%): 202 (58) [M$^+$], 187 (56), 159 (100), 145 (17), 131 (25), 115 (25), 104 (9).

COMPARISON EXAMPLE 1: 5-ISOBUTYL-2-METHYL-2,3-DIHYDRO-1H-INDEN-1-ONE

The title compound was prepared, following the general procedure C as described in Example 1. 7-Bromo-2-methyl- 2,3-dihydro-1H-inden-1-one and 5-bromo-2-methyl-2,3-dihydro-1H-inden-1-one (mixture of two isomers, ratio=15: 85, 4.00 g, 17.77 mmol), isobutylboronic acid (3.63 g, 35.5 mmol), potassium carbonate (7.37 g, 53.3 mmol), palladium (II) acetate (0.140 g, 0.533 mmol) and 1,1'-bis(diphenylphosphino)ferrocene (dppf ligand: 0.369 g, 0.666 mmol) in toluene (100 mL) were reacted at reflux under argon atmosphere for 2 h to give 5-isobutyl-2-methyl-2,3-dihydro-1H-inden-1-one as a colorless liquid (2.67 g, 74% yield) and 7-isobutyl-2-methyl-2,3-dihydro-1-inden-1-one as a colorless liquid (0.54 g, 15% yield).

Odor description: fruity fatty citrus green, fruity citral green, soapy $^1$H NMR (300 MHz, CDCl$_3$): δ=7.65 (d, J=7.8 Hz, 1H), 7.21 (s, 1H), 7.14 (d, J=7.8 Hz, 1H), 3.35 (dd, J=18.0, 8.7 Hz, 1H), 2.65-2.71 (m, 2H), 2.54 (d, J=7.2 Hz, 2H), 1.86-1.95 (m, 1H), 1.29 (d J=7.2 Hz, 3H), 0.92 (d, J=6.6 Hz, 6H) ppm; $^{13}$C NMR (75 MHz, CDCl$_3$): δ=208.9 (s), 153.8 (s), 149.5 (s), 134.3 (s), 128.6 (d), 126.9 (d), 123.6 (d), 45.7 (t), 42.1 (d), 34.8 (t), 30.2 (d), 22.312 (q), 16.3 (q) ppm; GC/MS (EI): m/z (%): 202 (75) [M$^+$], 187 (55), 160 (100), 146 (65), 115 (31), 91 (17).

COMPARISON EXAMPLE 2: 2-METHYL-5-PROPYL-2,3-DIHYDRO-1H-INDEN-1-ONE AND 2-METHYL-7-PROPYL-2,3-DIHYDRO-1H-INDEN-1-ONE

The title compound was prepared, following the general procedure C as described in Example 1. 7-Bromo-2-methyl-2,3-dihydro-1H-inden-1-one and 5-bromo-2-methyl-2,3-dihydro-1H-inden-1-one (mixture of two isomers, ratio=15: 85, 4.00 g, 17.77 mmol), propylboronic acid (3.63 g, 35.5 mmol), potassium carbonate (7.37 g, 53.3 mmol), palladium (II) acetate (0.140 g, 0.533 mmol) and dppf (0.369 g, 0.666 mmol) in toluene (100 mL) were reacted at reflux under argon atmosphere for 2 h to give 2-methyl-5-propyl-2,3-dihydro-1H-inden-1-one as a colorless liquid (2.30 g, 69% yield) and 2-methyl-7-propy-2,3-dihydro-1-inden-1-one as a colorless liquid (0.60 g, 18% yield).

2-methyl-7-propyl-2,3-dihydro-1H-inden-1-one: $^1$H NMR (300 MHz, CDCl$_3$): δ=7.40-7.45 (m, 1H), 7.24 (d, J=7.5 Hz, 1H), 7.10 (d, J=7.5 Hz, 1H), 3.28-3.37 (m, 1H), 2.99-3.05 (m, 2H), 2.62-2.72 (m, 2H), 1.58-1.67 (m, 2H), 1.29 (d, J=6.9 Hz, 3H), 0.97 (t, J=7.2 Hz, 3H) ppm; $^{13}$C NMR (75 MHz, CDCl$_3$): δ=209.9 (s), 154.3 (s), 143.9 (s), 133.9 (d), 133.3 (s), 128.3 (d), 123.9 (d), 42.3 (d), 34.6 (t), 33.6 (t), 24.1 (t), 16.3 (q), 14.0 (q) ppm; GC/MS (EI): m/z (%): 188 (70) [M$^+$], 173 (100), 160 (55), 145 (39), 128 (17), 115 (30), 91 (17).

Odor description (7-propyl): floral, rose, metallic 2-methyl-5-propyl-2,3-dihydro-1H-inden-1-one: $^1$H NMR (300 MHz, CDCl$_3$): δ=7.66 (d, J=7.8 Hz, 1H), 7.24 (s, 1H), 7.17 (d, J=7.8 Hz, 1H), 3.31-3.40 (m, 1H), 2.63-2.72 (m, 4H), 1.61-1.73 (m, 2H), 1.30 (d, J=7.2 Hz, 3H), 0.96 (t, J=7.2 Hz, 3H) ppm; $^{13}$C NMR (75 MHz, CDCl$_3$): δ=208.9 (s), 153.9 (s), 150.5 (s), 134.3 (s), 128.1 (d), 126.3 (d), 123.8 (d), 42.1 (d), 38.4 (t), 34.9 (t), 24.4 (t), 16.4 (q), 13.8 (q) ppm; GC/MS (EI): m/z (%): 188 (48) [M$^+$], 173 (100), 159 (28), 145 (19), 131 (20), 115 (20), 91 (12).

Odor description (5-propyl): green, waxy, fatty.

COMPARISON EXAMPLE 3: 2-METHYL-4-PROPYL-2,3-DIHYDRO-1H-INDEN-1-ONE

The title compound was prepared, following the general procedure C as described in Example 1. 4-Bromo-2-methyl-2,3-dihydro-1H-inden-1-one (1.50 g, 3.66 mmol), propylboronic acid (1.17 g, 13.3 mmol), potassium carbonate (2.76 g, 20.0 mmol), palladium (II) acetate (0.075 g, 0.333 mmol) and dppf (0.222 g, 0.400 mmol) in toluene (30 mL) were reacted at reflux under argon atmosphere for 2 h to give 2-methyl-4-propyl-2,3-dihydro-1H-inden-1-one as a colorless liquid (1.05 g, 84% yield).

Odor description: very weak, fruity, floral.

$^1$H NMR (300 MHz, CDCl$_3$): δ=7.59 (d, J=7.5 Hz, 1H), 7.39 (d, J=7.2 Hz, 1H), 7.27-7.32 (m, 1H), 3.34 (dd, J=16.5, 7.2 Hz, H), 2.59-2.72 (m, 4H) 1.60-1.73 (m, 2H), 1.31 (d, J=7.5 Hz, 3H), 0.99 (t, J=7.2 Hz, 3H) ppm; $^{13}$C NMR (75 MHz, CDCl$_3$): δ=209.7 (s), 151.9 (s), 140.2 (s), 136.2 (s), 134.3 (d), 127.6 (d), 121.4 (d), 41.8 (d), 34.0 (t), 33.5 (t), 23.0 (t), 18.3 (q), 14.0 (q) ppm; GC/MS (EI): m/z (%): 188 (73) [M$^+$], 173 (100), 159 (80), 145 (35), 131 (28), 115 (35), 91 (25).

COMPARISON EXAMPLE 4: 2-METHYL-5-(2-METHYLALLYL)-2,3-DIHYDRO-1H-INDEN-1-ONE AND 2-METHYL-7-(2-METHYLALLYL)-2,3-DIHYDRO-1H-INDEN-1-ONE

Using similar procedure as described in Example 22, Cesium carbonate (7.60 g, 23.3 mmol), palladium (II) acetate (0.175 g, 0.78 mmol), triphenylphosphine (0.82 g, 3.11 mmol), 3-Isopropyl-2,5-dimethylhex-5-en-3-ol (318 g, 18.7 mmol) and 7-bromo-2-methyl-2,3-dihydro-1H-inden-1-one and 5-bromo-2-methyl-2,3-dihydro-1H-inden-1-one (mixture of two isomers, ratio=15: 85, 3.50 g: 15.6 mmol) in toluene (80 mL) were reacted at reflux under argon atmosphere for 2 h to give 2-methyl-5-(2-methylallyl)-2,3-dihydro-1H-inden-1-one (222 g, 71% yield, colorless liquid) and 2-methyl-7-(2-methylallyl)-2:3-dihydro-1H-inden-1-one (0.41 g, 13% yield, colorless liquid).

2-Methyl-5-(2-methylallyl)-2,3-dihydro-1H-inden-1-one: $^1$H NMR (300 MHz, CDCl$_3$): δ=7.88 (d, J=1.8 Hz, 1H), 7.27 (s, 1H), 7.21 (d, J=7.8 Hz, 1H), 4.86 (s, 1H), 4.77 (s, 1H), 3.39 (s, 2H), 3.33-3.41 (m, 1H), 2.67-2.73 (m, 2H), 1.69 (s, 3H), 1.31 (d, J=7.2 Hz, 4H) ppm; $^{13}$C NMR (75 MHz, CDCl$_6$): δ=209.1 (s), 154.0 (s), 147.5 (s), 144.2 (s), 134.7 (s), 128.5 (d), 126.7 (d), 123.9 (d), 112.8 (t), 45.0 (t), 42.2 (d), 34.9 (t) 22.1 (q), 16.4 (q) ppm; GC/MS (EI): m/z (%): 200 (55) [M$^+$], 185 (100), 172 (48), 15(71), 143 (72), 129 (60), 115 (53), 91 (17).

Odor description: fatty fruity citrus floral, "citral myraldyl"-like, soapy.

2-methyl-7-(2-methylallyl)-2,3-dihydro-1H-inden-1-one: $^1$H NMR (300 MHz, CDCl$_3$): δ=7.47 (dd, J=7.5, 7.5 Hz, 1H), 7.29 (d, J=7.5 Hz, 1H), 7.15 (d, J=7.5 Hz, 1H), 4.79 (s, 1H), 4.57 (s, 1H), 3.75-3.91 (m, 2H), 3.30-3.39 (m, 1H), 2.63-2.72 (m, 2H), 1.75 (s, 3H), 1.29 (d, J=7.2 Hz, 3H) ppm; $^{13}$C NMR (75 MHz, CDCl$_3$): δ=209.9 (s), 154.2 (s), 144.9 (s), 140.6 (s), 134.0 (d), 133.6 (s), 128.8 (d), 124.3 (d), 111.7 (t), 42.4 (d), 38.6 (t), 34.5 (t) 22.7 (q), 16.3 (q) ppm; GC/MS (EI): m/z (%): 200 (30) [M$^+$], 185 (100), 167 (11), 143 (10), 115 (22), 91 (7).

Odor description: green, wax, slightly minty.

COMPARISON EXAMPLE 5: 2-METHYL-4-(2-METHYLALLYL)-2,3-DIHYDRO-1H-INDEN-1-ONE

The title compound was prepared, following the general as described in Example 22. Cesium carbonate (3.26 g, 10.0 mmol), palladium (II) acetate (0.075 g, 0.33 mmol), triphenylphosphine (0.35 g, 1.33 mmol), 3-isopropyl-2,5-dimethylhex-5-en-3-ol (1.36 g, 8.00 mmol) and 4-bromo-2-methyl-2,3-dihydro-1H-inden-1-one (1.50 g, 6.66 mol) in toluene (35 mL) were reacted at reflux under argon atmosphere for 2 h to give 2-methyl-4-(2-methylallyl)-2,3-dihydro-1H-inden-1-one as a colorless liquid (1.12 g, 84% yield).

$^1$H NMR (300 MHz, CDCl$_3$): δ=7.65 (d, J=7.5 Hz, 1H), 7.41 (d, J=7.5 Hz, 1H), 7.34 (dd, J=7.5, 7.5 Hz, 1H), 4.85 (s, 1H), 4.63 (s, 1H), 3.38 (s, 2H), 3.30-3.38 (m, 1H), 2.68-2.74 (m, 1H), 2.62 (dd, J=17.1, 3.9 Hz, 1H), 1.73 (s, 3H), 1.31 (d, J=7.5 Hz, 3H) ppm; $^{13}$C NMR (75 MHz, CDCl$_3$): δ=209.8 (s), 152.7 (s), 143.1 (s), 137.2 (s), 136.4 (s), 135.2 (d), 127.7 (d), 122.0 (d), 112.4 (t), 41.9 (d), 40.7 (t), 33.5 (t), 22.4 (q), 16.4 (q) ppm; GC/MS (EI): m/z (%): 200 (100) [M$^+$], 185 (65), 157 (60), 143 (42), 115 (47), 91 (13).

Odor description: fruity floral metallic, myradyl-like.

COMPARISON EXAMPLE 6: 5-CYCLOPROPYL-2-METHYL-2,3-DIHYDRO-1H-INDEN-1-ONE, AND 7-CYCLOPROPYL-2-METHYL-2,3-DIHYDRO-1H-INDEN-1-ONE

The title compound was prepared, following the general procedure C as described in Example 1. 7-Bromo-2-methyl-2,3-hydro-1H-inden-1-one and 5-bromo-2-methyl-2,3-dihydro-1H-inden-1-one (mixture of two isomers, ratio=15:85, 3.00 g, 13.33 mmol), cyclopropylboronic acid (2.29 g, 26.7 mmol), potassium carbonate (5.53 g, 40.0 mmol), palladium (II) acetate (0.120 g, 0.533 mmol) and 1,1'-bis(diphenylphosphino)ferrocene (dppf ligand, 0.389 g, 0.666 mmol) in toluene (100 ml) were reacted at reflux under argon atmosphere for 2 h followed by distillation through Kugelrohr to give 5-cyclopropyl-2-methyl-2,3-dihydro-1H-inden-1-one (140° C./0.11 mbar) as a colorless liquid (2.02 g, 81% yield) and 7-cyclopropyl-2-methyl-2,3-dihydro-1H-inden-1-one (130° C./0.11 mbar) as a colorless liquid (0.300 g, 12% yield).

5-Cyclopropyl-2-methyl-2,3-dihydro-1H-inden-1-one:
$^1$H NMR (300 MHz, CDCl$_3$): δ=7.61 (d, J=8.1 Hz, 1H), 7.08 (s, 1H), 7.02 (d, J=7.8 Hz, 1H), 3.27-3.36 (m, 1H), 2.60-2.70 (m, 2H), 1.92-1.97 (m, 1H), 1.28 (d, J=7.2 Hz, 3H), 1.03-1.10 (m, 2H), 1.77-1.80 (m, 2H) ppm; $^{13}$C NMR (75 MHz, CDCl$_3$): δ=208.6 (s), 153.9 (s), 152.4 (s), 134.0 (s), 125.0 (d), 123.8 (d), 122.9 (d), 42.1 (d), 34.8 (t), 16.4 (q), 16.1 (d), 10.6 (t), 10.6 (t) ppm; GC/MS (EI): m/z (%): 186 (50) [M$^+$], 171 (100), 158 (10), 143 (19), 128 (31), 115 (33).

Odor description: green, creamy, lactonic.

7-Cyclopropyl-2-methyl-2,3-dihydro-1H-inden-1-one:
$^1$H NMR (300 MHz, CDCl$_3$) δ=7.36-7.41 (m, 1H), 7.15 (d, J=7.5 Hz, 1H), 6.71 (d, J=7.5 Hz, 1H), 3.25-3.34 (m, 2H), 2.60-2.70 (m, 2H), 1.30 (d, J=7.2 Hz, 3H), 1.05-1.10 (m, 2H), 0.72-0.76 (m, 2H) ppm; $^{13}$C NMR (75 MHz, CDCl$_3$): δ=210.4 (s), 154.0 (s), 146.1 (s), 134.3 (d), 133.5 (s), 122.9 (d), 121.0 (d), 42.2 (d), 34.4 (t), 18.4 (q), 10.7 (t), 10.6 (t), 10.0 (d) ppm; GC/MS (EI): m/z (%): 186 (30) [M$^+$], 171 (100), 153 (9), 141 (12), 128 (31), 115 (28).

Odor description: green, floral, leathery.

COMPARISON EXAMPLE 7: 4-CYCLOPROPYL-2-METHYL-2,3-DIHYDRO-1H-INDEN-1-ONE

The title compound was prepared, following the general procedure C as described in Example 1. 4-Bromo-2-methyl-2,3-dihydro-1H-inden-1-one (1.50 g, 6.66 mmol), cyclopropylboronic acid (1.15 g, 13.33 mmol), potassium carbonate (2.78 g, 19.99 mmol), palladium (II) acetate (0.075 g, 0.333 mmol) and 1,1'-bis(diphenylphosphino)ferrocene (dppf ligand, 0.222 g, 0.400 mmol) in toluene (30 ml) were reacted at reflux under argon atmosphere for 2 h followed by distillation through Kugelrohr (125° C./0.08 mbar) to give to give 4-cyclopropyl-2-methyl-2,3-dihydro-1H-inden-1-one as a colorless liquid (1.11 g, 89% yield).

$^1$H NMR (300 MHz, CDCl$_3$): δ=7.54 (d, J=7.5 Hz, 1H), 7.24-7.29 (m, 1H), 7.09 (d, J=7.5 Hz, 1H), 3.45 (dd, J=17.7, 8.7 Hz, 1H), 2.67-2.76 (m, 2H), 1.88-1.97 (m, 1H), 1.33 (d, J=7.2 Hz, 3H), 0.99-1.05 (m, 2H), 0.71-0.74 (m, 2H) ppm; $^{13}$C NMR (75 MHz, CDCl$_3$): δ=209.7 (s), 152.9 (s), 141.3 (s), 136.9 (s), 129.5 (d), 127.7 (d), 120.9 (d), 41.8 (d), 33.6 (t), 16.4 (q), 11.7 (q), 7.9*2 (t) ppm; GC/MS (EI): m/z (%): 186 (100) [M$^+$], 171 (71), 157 (29), 143 (85), 128 (91), 115 (65), 91 (11).

Odor description: weak floral.

EXAMPLE 24: DETERMINATION OF GC-ODOR THRESHOLD VALUES

According to standard procedures known to the person skilled in the art, threshold values for volatile perfumery compounds are determined on a gas chromatograph equipped with a sniff port by a panel of trained evaluators. The lowest concentration smelled by each panelist is recorded as the individual threshold value expressed in ng (absolute amount of compound delivered at the sniff port).

Under identical conditions the odor threshold value for the individual compounds was measured. The results are given below.

| Compound | odor threshold value [ng] |
|---|---|
| 6-isobutyl-2-methyl-2,3-dihydro-1H-inden-1-one | 0.06 |
| 5-isobutyl-2-methyl-2,3-dihydro-1H-inden-1-one | 1.56 |
| 2-methyl-6-propyl-2,3-dihydro-1H-inden-1-one | 0.04 |
| 2-methyl-5-propyl-2,3-dihydro-1H-inden-1-one | 0.98 |
| 2-methyl-4-propyl-2,3-dihydro-1H-inden-1-one | 6.25 |
| 2-methyl-6-(2-methylallyl)-2,3-dihydro-1H-inden-1-one | 0.24 |
| 2-methyl-7-(2-methylallyl)-2,3-dihydro-1H-inden-1-one | 4.96 |
| 2-methyl-4-(2-methylallyl)-2,3-dihydro-1H-inden-1-one | 6.25 |
| 6-Cyclopropyl-2-methyl-2,3-dihydro-1H-inden-1-one | 0.46 |
| 7-Cyclopropyl-2-methyl-2,3-dihydro-1H-inden-1-one | 4.31 |
| 4-Cyclopropyl-2-methyl-2,3-dihydro-1H-inden-1-one | 31.7 |

As can be seen from the results above the compounds of the present invention (C-6 substituted indanone derivatives) have an odor threshold value which is at least about 10 times lower compared to the compounds substituted at C-4, C-5 or C-7 position. Based on this, a significant advance is achieved because much smaller amount of the claimed compounds is required to impart the same odor intensity.

EXAMPLE 25: ROSY FRAGRANCE COMPOSITION FOR FINE PERFUMERY

| Compound/Ingredient | parts by weight 1/1000 |
|---|---|
| Beta Ionone | 1 |
| Linalool | 3 |
| 2-Cis-3,7-Dimethyl-2,6-Octadien-1-ol (Nerolex) | 30 |
| Citronellol | 40 |
| Rhodinol ™ | 60 |
| Geraniol | 80 |
| Phenyl ethyl alcohol | 302 |
| 3,7-Dimethyl-6-octenal (Citronellal) @ 10% DPG | 2 |

-continued

| Compound/Ingredient | parts by weight 1/1000 |
|---|---|
| 3,7-Dimethylocta-2,6-dienal (Citral Lemarome N) | 3 |
| 3,7-Dimethyl-6-octen-1-yl acetate (Citronellyl acetate) | 5 |
| Neryl acetate (CAS 141-12-8) | 5 |
| Geranyl acetate (CAS 105-87-3) | 15 |
| Methyl phenyl acetate | 2 |
| Benzyl Methyl Ether @ 10% DPG | 2 |
| 2-Phenylethyl 2-methylbutyrate (Anatolyl ™) | 3 |
| 2-Phenylethyl 2-phenylacetate | 5 |
| 2-Phenylethyl acetate | 15 |
| 3,7-Dimethyl-1,3,6-octatriene (Ocimene) | 1 |
| Caryophyllene (CAS 87-44-5) | 2 |
| Eugenol | 10 |
| n-Octanal (food grade) @10% DPG | 1 |
| n-Nonanal (food grade) @ 10% DPG | 2 |
| 4-Methyl-2-(2-methylprop-1-enyl)tetrahydro-2H-pyran (Rose Oxyde CO) | 3 |
| n-Hexyl acetate @ 10% DPG | 2 |
| cis-3-Hexenol @ 10% DPG | 3 |
| cis-3-Hexenyl acetate @ 10% DPG | 4 |
| 1-(2,6,6-Trimethyl-1,3-cyclohexadien-1-yl)-2-buten-1-one (Damascenone @ 1% DPG) | 7 |
| Beta Damascone @ 1% DPG | 7 |
| Dipropylen glycol (DPG) | 375 |
| 6-isobutyl-2-methyl-2,3-dihydro-1H-inden-1-one (Example 1) | 10 |
| Total: | 1000 |

This natural rose, spicy (clove) fresh light and delicate accord with slightly fruity (apple) facets is best to be assessed at 10 weight % in alcohol (85). The addition of 6-isobutyl-2-methyl-2,3-dihydro-1H-inden-1-one results in a much more impact accord, and the character is now fruity peach creamy, with a rose floral freshness. The accord has now more body, and is more long lasting compared to an accord without wherein the compound of formula (I) is replaced by DPG. This accord above is, e.g., suitable for fragrancing a softener.

The invention claimed is:

1. A fragrance composition comprising as odorant a compound of formula (I)

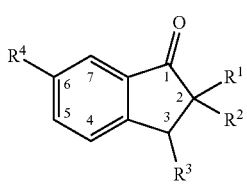

(I)

wherein
R$^1$ is selected from hydrogen, methyl and ethyl;
R$^2$ is selected from hydrogen, methyl and ethyl, and R$^3$ is selected from hydrogen and methyl; or
R$^2$ and R$^3$ form together with the carbon atoms to which they are attached C$_3$-C$_5$ cycloalkyl;
R$^4$ is selected from C$_2$-C$_5$ alkyl, C$_2$-C$_5$ alkenyl, C$_1$-C$_4$ alkoxy, C$_3$-C$_5$ cycloalkyl, and C$_3$-C$_6$ cycloalkenyl;
or a mixture thereof; and a base material.

2. The fragrance composition according to claim 1 wherein the base material is selected from odorant molecules and auxiliary agents.

3. A fragranced article comprising as odorant a compound of formula (I)

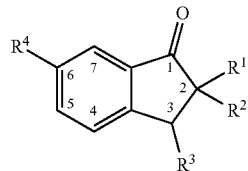

(I)

wherein
R$^1$ is selected from hydrogen, methyl and ethyl;
R$^2$ is selected from hydrogen, methyl and ethyl, and R$^3$ is selected from hydrogen and methyl; or
R$^2$ and R$^3$ form together with the carbon atoms to which they are attached C$_3$-C$_5$ cycloalkyl;
R$^4$ is selected from C$_2$-C$_5$ alkyl, C$_2$-C$_5$ alkenyl, C$_1$-C$_4$ alkoxyl, C$_3$-C$_5$ cycloalkyl, and C$_3$-C$_6$ cycloalkenyl;
or a mixture thereof; and a consumer product base.

4. The fragranced article according to claim 3 wherein the consumer product base is selected from fine fragrance, household products, laundry products, body care products, cosmetic products and air care products.

5. The fragranced article according to claim 1, comprising 0.00001 weight % to 90 weight % of the compound of formula (I), or a mixture thereof, based on the total weight of the article.

6. The fragranced article according to claim 3 comprising at least one compound of formula (I), or a mixture thereof, and at least one ingredient selected from the group consisting of a carrier material and fragrance ingredients.

7. A method of Improving, enhancing or modifying a consumer product base comprising adding to the consumer product base an olfactory acceptable amount of a compound of formula (I)

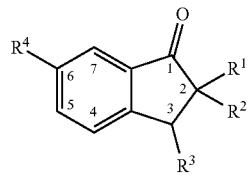

(I)

wherein
R$^1$ is selected from hydrogen, methyl and ethyl;
R$^2$ is selected from hydrogen, methyl and ethyl, and R$^3$ is selected from hydrogen and methyl; or
R$^2$ and R$^3$ form together with the carbon atoms to which they are attached C$_3$-C$_5$ cycloalkyl;
R$^4$ is selected from C$_2$-C$_5$ alkyl, C$_2$-C$_5$ alkenyl, C$_1$-C$_4$ alkoxy, C$_3$-C$_5$ cycloalkyl, and C$_3$-C$_6$ cycloalkenyl;
or a mixture thereof.

8. The method according to claim 7, wherein the consumer product base is selected from the group consisting of fine fragrance, household products, laundry products, body care products, cosmetic products and air care products.

9. A compound of formula (I)

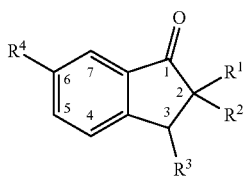

wherein
R¹ is selected from methyl and ethyl;
R² is hydrogen, and R³ is hydrogen; or
R² and R³ form together with the carbon atoms to which they are attached $C_3$-$C_5$ cycloalkyl;
R⁴ is selected from $C_3$-$C_5$ alkyl, $C_2$-$C_5$ alkenyl, $C_3$-$C_4$ alkoxy, $C_3$-$C_5$ cycloalkyl, and $C_3$-$C_6$ cycloalkenyl with the proviso that R⁴ is not isopropyl or tert-butyl.

10. The fragranced article according to claim 3, comprising 0.00001 weight % to 90 weight % of the compound of formula (I), or a mixture thereof, based on the total weight of the article.

11. The fragranced article according to claim 3, wherein the compound of formula (I) is at least one selected from the group consisting of:
3-methyl-6-propyl-2,3-dihydro-1H-Linden-1-one;
6-isobutyl-2,3-dihydro-1H-Inden-1-one;
6-isopropyl-2-methyl-2,3-dihydro-1H-inden-1-one;
6-(tert-butyl)-2-methyl-2,3-dihydro-1H-inden-1-one;
2,3-dimethyl-6-propyl-2,3-dihydro-1H-inden-1-one;
2-methyl-6-propyl-2,3-dihydro-1H-inden-1-one;
6-isobutyl-3-methyl-2,3-dihydro-1H-inden-1-one;
6-isobutyl-2,2-dimethyl-2,3-dihydro-1H-inden-1-one;
6-(tert-butyl)-3-methyl-2,3-dihydro-1H-inden-1-one;
6-cyclopropyl-2-methyl-2,3-dihydro-1H-inden-1-one;
6-cyclopentyl-2-methyl-2,3-dihydro-1H-inden-1-one;
2-ethyl-6-isobutyl-2,3-dihydro-1H-inden-1-one;
6-ethyl-2-methyl-2,3-dihydro-1H-inden-1-one;
6-isopentyl-2-methyl-2,3-dihydro-1H-inden-1-one;
6-ethoxy-2-methyl-2,3-dihydro-1H-inden-1-one;
6-isopropoxy-2-methyl-2,3-dihydro-1H-inden-1-one;
2-methyl-6-propoxy-2,3-dihydro-1H-inden-1-one;
6-isobutoxy-2-methyl-2,3-dihydro-1H-Inden-1-one;
4-isobutyl-6a-methyl-1a,6a-dihydrocyclopropa[a]inden-6(1H)-one;
2-methyl-6-(2-methylallyl)-2,3-dihydro-1H-inden-1-one; and
6-butyl-2-methyl-2,3-dihydro-1H-linden-1-one.

12. The fragrance composition according to claim 1, wherein the compound of formula (I) is at least one selected from the group consisting of:
3-methyl-6-propyl-2,3-dihydro-1H-inden-1-one;
6-isobutyl-2,3-dihydro-1H-inden-1-one;
6-Isopropyl-2-methyl-2,3-dihydro-1H-inden-1-one;
6-(tert-butyl)-2-methyl-2,3-dihydro-1H-inden-1-one;
2,3-dimethyl-6-propyl-2,3-dihydro-1H-inden-1-one;
2-methyl-6-propyl-2,3-dihydro-1H-inden-1-one;
6-isobutyl-3-methyl-2,3-dihydro-1H-inden-1-one;
6-isobutyl-2,2-dimethyl-2,3-dihydro-1H-inden-1-one;
6-(tort-butyl)-3-methyl-2,3-dihydro-1H-inden-1-one;
6-cyclopropyl-2-methyl-2,3-dihydro-1H-inden-1-one;
6-cyclopentyl-2-methyl-2,3-dihydro-1H-inden-1-one;
2-ethyl-6-isobutyl-2,3-dihydro-1H-inden-1-one;
6-ethyl-2-methyl-2,3-dihydro-1H-inden-1-one;
6-isopentyl-2-methyl-2,3-dihydro-1H-Inden-1-one;
6-ethoxy-2-methyl-2,3-dihydro-1H-inden-1-one;
6-isopropoxy-2-methyl-2,3-dihydro-1H-inden-1-one;
2-methyl-6-propoxy-2,3-dihydro-1H-inden-1-one;
6-isobutoxy-2-methyl-2,3-dihydro-1H-inden-1-one;
4-isobutyl-6n-methyl-1a,6a-dihydrocyclopropa[a]inden-6(1H)-one;
2-methyl-6-(2-methylallyl)-2,3-dihydro-1H-Inden-1-one; and
6-butyl-2-methyl-2,3-dihydro-1H-inden-1-one.

13. The method according to claim 7, wherein the compound of formula (I) is at least one selected from the group consisting of:
3-methyl-6-propyl-2,3-dihydro-1H-inden-1-one;
6-isobutyl-2,3-dihydro-1H-inden-1-one;
6-isopropyl-2-methyl-2,3-dihydro-1H-inden-1-one;
6-(tert-butyl)-2-methyl-2,3-dihydro-1H-inden-1-one;
2,3-dimethyl-6-propyl-2,3-dihydro-1H-inden-1-one;
2-methyl-6-propyl-2,3-dihydro-1H-inden-1-one;
6-isobutyl-3-methyl-2,3-dihydro-1H-inden-1-one;
6-isobutyl-2,2-dimethyl-2,3-dihydro-1H-inden-1-one;
6-(tert-buty)-3-methyl-2,3-dihydro-1H-inden-1-one;
6-cyclopropyl-2-methyl-2,3-dihydro-1H-inden-1-one;
6-cyclopentyl-2-methyl-2,3-dihydro-1H-inden-1-one;
2-ethyl-6-isobutyl-2,3-dihydro-1H-inden-1-one;
6-ethyl-2-methyl-2,3-dihydro-1H-inden-1-one;
6-isopentyl-2-methyl-2,3-dihydro-1H-inden-1-one;
6-ethoxy-2-methyl-2,3-dihydro-1H-inden-1-one;
6-isopropoxy-2-methyl-2,3-dihydro-1H-inden-1-one;
2-methyl-6-propoxy-2,3-dihydro-1H-inden-1-one;
6-isobutoxy-2-methyl-2,3-dihydro-1H-inden-1-one;
4-isobutyl-6a-methyl-1a,6a-dihydrocyclopropa[a]inden-6(1H)-one;
2-methyl-6-(2-methylallyl)-2,3-dihydro-1H-inden-1-one; and
6-butyl-2-methyl-2,3-hydro-1H-inden-1-one.

* * * * *